United States Patent
Ganesan et al.

(10) Patent No.: US 8,697,386 B2
(45) Date of Patent: Apr. 15, 2014

(54) METHODS AND COMPOSITIONS FOR MODULATING HEPSIN ACTIVATION OF MACROPHAGE-STIMULATING PROTEIN

(75) Inventors: Rajkumar Ganesan, Germantown, MD (US); Daniel Kirchhofer, Los Altos, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/503,636

(22) PCT Filed: Oct. 21, 2010

(86) PCT No.: PCT/US2010/053600
§ 371 (c)(1),
(2), (4) Date: Jul. 12, 2012

(87) PCT Pub. No.: WO2011/050194
PCT Pub. Date: Apr. 28, 2011

(65) Prior Publication Data
US 2012/0282271 A1 Nov. 8, 2012

Related U.S. Application Data

(60) Provisional application No. 61/253,990, filed on Oct. 22, 2009.

(51) Int. Cl.
*C12Q 1/37* (2006.01)

(52) U.S. Cl.
USPC .......................................................... 435/24

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 4,708,871 A | 11/1987 | Geysen |
| 4,816,567 A | 3/1989 | Cabilly et al. |
| 4,833,092 A | 5/1989 | Geysen |
| 4,975,278 A | 12/1990 | Senter et al. |
| 5,223,409 A | 6/1993 | Ladner et al. |
| 5,229,275 A | 7/1993 | Goroff |
| 5,364,934 A | 11/1994 | Drayna et al. |
| 5,403,484 A | 4/1995 | Ladner et al. |
| 5,428,130 A | 6/1995 | Capon et al. |
| 5,545,806 A | 8/1996 | Lonberg et al. |
| 5,545,807 A | 8/1996 | Surani et al. |
| 5,556,762 A | 9/1996 | Pinilla et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,689 A | 11/1996 | Heuckeroth et al. |
| 5,571,894 A | 11/1996 | Wels et al. |
| 5,573,905 A | 11/1996 | Lerner et al. |
| 5,591,669 A | 1/1997 | Krimpenfort et al. |
| 5,641,870 A | 6/1997 | Rinderknecht et al. |
| 5,648,237 A | 7/1997 | Carter et al. |
| 5,663,143 A | 9/1997 | Ley et al. |
| 5,731,168 A | 3/1998 | Carter et al. |
| 5,739,277 A | 4/1998 | Presta et al. |
| 5,750,373 A | 5/1998 | Garrard et al. |
| 5,789,199 A | 8/1998 | Joly et al. |
| 5,837,234 A | 11/1998 | Gentile et al. |
| 5,840,523 A | 11/1998 | Simmons et al. |
| 5,869,046 A | 2/1999 | Presta et al. |
| 6,828,146 B2 | 12/2004 | Desnoyers et al. |
| 7,432,044 B2 | 10/2008 | Kirchhofer et al. |
| 8,124,352 B2 | 2/2012 | Kirchhofer et al. |
| 2011/0262452 A1 | 10/2011 | Ganesan et al. |
| 2012/0141374 A1 | 6/2012 | Kirchhofer et al. |

FOREIGN PATENT DOCUMENTS

| | | |
|---|---|---|
| EP | 0003089 B1 | 8/1981 |
| EP | 0600517 B1 | 8/2000 |
| EP | 1391213 A1 | 2/2004 |
| WO | 81/01145 A1 | 4/1981 |
| WO | 84/03506 | 9/1984 |
| WO | 84/03564 | 9/1984 |
| WO | 88/07378 A1 | 10/1988 |
| WO | 90/10048 A1 | 9/1990 |
| WO | 91/00360 A1 | 1/1991 |
| WO | 92/00373 A1 | 1/1992 |
| WO | 93/08829 A1 | 5/1993 |
| WO | 93/16185 A2 | 8/1993 |
| WO | 93/21232 A1 | 10/1993 |
| WO | 93/25673 A1 | 12/1993 |
| WO | 94/04690 A1 | 3/1994 |
| WO | 96/07321 A1 | 3/1996 |
| WO | 96/16673 A1 | 6/1996 |
| WO | 97/09446 | 3/1997 |
| WO | 97/17852 | 5/1997 |
| WO | 97/33551 | 9/1997 |
| WO | 98/02463 A1 | 1/1998 |
| WO | 00/00823 | 1/2000 |
| WO | 00/39585 A1 | 7/2000 |
| WO | 03/016484 A2 | 2/2003 |
| WO | 2004/033630 A2 | 4/2004 |
| WO | 2006/014928 A1 | 2/2006 |
| WO | 2007/149932 A2 | 12/2007 |
| WO | 2007/149935 A2 | 12/2007 |

OTHER PUBLICATIONS

Anderson et al., "Human Gene Therapy" Science 256(5058):808-813 (May 8, 1992).
Baldwin and Byers, "Monoclonal Antibodies in Cancer Treatment" Lancet 327(8481):603-605 (Mar. 15, 1986).
Barbas et al., "In Vitro Evolution of a Neutralizing Human Antibody to Human Immunodeficiency Virus Type 1 to Enhance Affinity and Broaden Strain Cross-Reactivity" P Natl Acad Sci USA 91(9):3809-3813 (Apr. 1994).
Beliveau et al., "Probing the substrate specificities of matriptase, matriptase-2, hepsin and DESC1 with internally quenched fluorescent peptides" FEBS J. 276(8):2213-26 ( 2009).

(Continued)

*Primary Examiner* — Marianne P Allen
(74) *Attorney, Agent, or Firm* — Stephanie Yonker

(57) ABSTRACT

The invention provides methods and compositions for modulating hepsin activity and the MSP/Ron pathway, in particular by regulating pro-MSP activation by hepsin.

10 Claims, 7 Drawing Sheets

(56) References Cited

OTHER PUBLICATIONS

Betsunoh et al., "Clinical relevance of hepsin and hepatocyte growth factor activator inhibitor type 2 expression in renal cell carcinoma" Cancer Sci. 98(4):491-8 (2007).
Bhatt et al., "Coordinate expression and functional profiling identify an extracellular proteolytic signaling pathway" Proc Natl Acad Sci U S A. 104(14):5771-6 (2007).
Brennan et al., "Preparation of bispecific antibodies by chemical recombination of monoclonal immunoglobulin G$_1$ fragments" Science 229:81-83 (1985).
Bruggemann et al., "Designer mice: the production of human antibody repertoires in transgenic animals" Year in Immunology 7:33-40 (1993).
Caron et al., "Engineered Humanized Dimeric Forms of IgG are More Effective Antibodies" J Exp Med 176:1191-1195 (Oct. 1992).
Carter et al., "High level *Escherichia coli* expression and production of a bivalent humanized antibody fragment" Bio/Tech 10:163-167 (Feb. 1992).
Carter et al., "Humanization of an anti-p185$^{HER2}$ antibody for human cancer therapy" Proc. Natl. Acad. Sci. USA 89:4285-4289 (May 1992).
Chothia and Lesk, "Canonical Structures for the Hypervariable Regions of Immunoglobulins" J Mol Biol 196(4):901-917 (Aug. 20, 1987).
Clackson et al., "Making antibody fragments using phage display libraries" Nature 352:624-628 (Aug. 15, 1991).
Cwirla et al., "Peptides on phage: a vast library of peptides for identifying ligands" P Natl Acad Sci USA 87:6378-6382 (Aug. 1990).
Dhanasekaran et al., "Delineation of prognostic biomarkers in prostate cancer" Nature 412(6849):822-826 (Aug. 23, 2001).
Doronina et al., "Development of potent monoclonal antibody auristatin conjugates for cancer therapy" Nat Biotechnol 21(7):778-784 (Jul. 2003).
Geysen et al., "Small peptides induce antibodies with a sequence and structural requirement for binding antigen comparable to antibodies raised against the native protein" P Natl Acad Sci USA 82:178-182 (1985).
Geysen et al., "Strategies for epitope analysis using peptide synthesis" J Immunol Methods 102:259-274 (1987).
Geysen et al., "The delineation of peptides able to mimic assembled epitopes" Ciba Found Symp. 119:130-49 (1986).
Geysen et al., "Use of peptide synthesis to probe viral antigens for epitopes to a resolution of a single amino acid" P Natl Acad Sci USA 81:3998-4002 (1984).
Griffiths et al., "Human anti-self antibodies with high specificity from phage display libraries" EMBO J 12(2):725-734 (1993).
Gruber et al., "Efficient tumor cell lysis mediated by a bispecific single chain antibody expressed in *Escherichia coli*" J Immunol. 152:5368-5374 (1994).
Haab, "Antibody arrays in cancer research" Mol Cell Proteomics 4(4):377-383 (2005).
Harris, "Production of humanized monoclonal antibodies for in vivo imaging and therapy" Biochem. Soc. Trans. 23(4):1035-1038 (Nov. 1995).
Hawkins et al., "Selection of Phage Antibodies by Binding Affinity Mimicking Affinity Maturation" J Mol Biol 226:889-896 (1992).
Herter et al., "Hepatocyte growth factor is a preferred in vitro substrate for human hepsin, a membrane-anchored serine protease implicated in prostate and ovarian cancers" Biochemical Journal Immediate Publication, Online Apr. 20, 2005, Retrived from the Internet: URL:www.biochemj.org/bj/imps_x/pdf/BJ20041955.pdf:1-43.
Herter et al., "Hepatocyte growth factor is a preferred in vitro substrate for human hepsin, a membrane-anchored serine protease implicated in prostate and ovarian cancers" Biochem J 390:125-136 (2005).
Hess et al., "Cooperation of glycolytic enzymes" Adv Enzyme Regul. 7:149-67 (1969).
Hinman et al., "Preparation and characterization of monoclonal antibody conjugates of the calicheamicins: a novel and potent family of antitumor antibiotics" Cancer Res. 53:3336-3342 (Jul. 15, 1993).
Hitzeman et al., "Isolation and Characterization of the Yeast 3-Phosphoglycerokinase Gene (PGK) by an Immunological Screening Technique" J Biol Chem. 255(24):12073-80 (Dec. 25, 1980).
Holland and Holland, "Isolation and Identification of Yeast Messenger Ribonucleic Acids Coding for Enolase, Glyceraldehyde-3-phosphate Dehydrogenase, and Phosphoglycerate Kinase" Biochemistry 17(23):4900-7 (1978).
Holliger et al., "'Diabodies': small bivalent and bispecific antibody fragments" Proc. Natl. Acad. Sci. USA 90:6444-6448 (Jul. 1993).
Hurle and Gross, "Protein engineering techniques for antibody humanization" Curr. Opin. Biotechnol. 5:428-433 (1994).
Jackson et al., "In vitro antibody maturation. Improvement of a high affinity, neutralizing antibody against IL-1$_\beta$" J Immunol 154(7):3310-3319 (1995).
Jakobovits et al., "Analysis of homozygous mutant chimeric mice: deletion of the immunoglobulin heavy-chain joining region blocks B-cell development and antibody production" Proc. Natl. Acad. Sci. USA 90:2551-2555 (Mar. 1993).
Jakobovits et al., "Germ-line transmission and expression of a human-derived yeast artificial chromosome" Nature 362:255-258 (Mar. 18, 1993).
Johnson, et al. et al., "Human Antibody Engineering" Curr Opin Struc Biol 3:564-571 (1993).
Jones et al., "Replacing the complementarity-determining regions in a human antibody with those from a mouse" Nature 321:522-525 (May 1986).
Kang et al., "Linkage of recognition and replication functions by assembling combinatorial antibody Fab libraries along phage surfaces" P Natl Acad Sci USA 88(10):4363-4366 (May 15, 1991).
Kawaguchi et al. et al., "Hepatocyte growth factor activator is a serum activator of single-chain precursor macrophage-stimulating protein" FEBS Lett 276(13):3481-90 (2009).
Kazama et al., "Hepsin, a putative membrane-associated serine protease, activates human factor VII and initiates a pathway of blood coagulation on the cell surface leading to thrombin formation" J Biol Chem. 270(1):66-72 (Jan. 6, 1995).
Kirchhofer et al., "Hepsin activates pro-hepatocyte growth factor and is inhibited by hepatocyte growth factor activator inhibitor-1B (HAI-1B) and HAI-2" FEBS Lett. 579(9):1945-50 (Mar. 28, 2005).
Kirchhofer et al., "Tissue expression, protease specificity, and Kunitz domain functions of hepatocyte growth factor activator inhibitor-1B (HAI-1B), a new splice variant of HAI-1" J Biol Chem 278(38):36341-36349 (Sep. 19, 2003).
Kostelny et al., "Formation of a bispecific antibody by the use of leucine zippers" J Immunol. 148:1547-1553 (Mar. 1, 1992).
Kozbor et al., "A human hybrid myeloma for production of human monoclonal antibodies" J Immunol. 133(6):3001-3005 (Dec. 1984).
Landers et al., "Use of multiple biomarkers for a molecular diagnosis of prostate cancer" Int J Cancer 114(6):950-6 (2005).
Leonard et al., "Macrophage stimulating protein" Adv Cancer Res. 77:139-67 (2000).
Liu et al., "Eradication of large colon tumor xenografts by targeted delivery of maytansinoids" Proc. Natl. Acad. Sci. USA 93:8618-8623 (Aug. 1996).
Lode et al., "Targeted therapy with a novel enediyene antibiotic calicheamicin $\theta^I_1$ effectively suppresses growth and dissemination of liver metastases in a syngeneic model of murine neuroblastoma" Cancer Res. 58:2925-2928 (Jul. 15, 1998).
Lokker et al., "Structure-Function Analysis of Hepatocyte Growth Factor: Identification of Variants that Lack Mitogenic Activity Yet Retain High Affinity Receptor Binding" EMBO J 11(7):2503-2510 (1992).
Lowman et al., "Selecting High-Affinity Binding Proteins by Monovalent Phage Display" Biochemistry—US 30(45):10832-10838 (1991).
Luo et al., "Human prostate cancer and benign prostatic hyperplasia: molecular dissection by gene expression profiling" Cancer Res 61(12):4683-4688 (Jun. 15, 2001).
Magee et al., "Expression profiling reveals hepsin overexpression in prostate cancer" Cancer Res 61(15):5692-5696 (Aug. 1, 2001).

(56) References Cited

OTHER PUBLICATIONS

Mandler et al., "Immunoconjugates of geldanamycin and Anti-HER2 monoclonal antibodies: antiproliferative activity on human breast carcinoma cell lines" J. National Cancer Institute 92(19):1573-1581 (Oct. 4, 2000).
Mandler et al., "Modifications in synthesis strategy improved the yield and efficacy of geldanamycin-herceptin immunoconjugates" Bioconjugate Chem. 13:786-791 ( 2002).
Mandler et al., "Synthesis and evaluation of antiproliferative activity of a Geldanamycin-Herceptin™ immunoconjugate" Bioorg. Med. Chem. Lett. 10:1025-1028 (2000).
Marasco et al., "Design, intracellular expression, and activity of a human anti-human immunodeficiency virus type 1 gp 120 single-chain antibody" P Natl Acad Sci USA 90:7889-7893 (Aug. 1993).
Marks et al., "By-passing immunization, Human antibodies from V-gene libraries displayed on phage" J. Mol. Biol. 222:581-597 ( 1991).
Marks et al., "By-passing immunization: building high affinity human antibodies by chain shuffling" Bio/Technology 10:779-783 (Jul. 1992).
Massey, "Catalytic antibodies catching on" Nature 328:457-458 (Jul. 1987).
Matsuo et al., "Expression of the serine protease hepsin and clinical outcome of human endometrial cancer" Anticancer Res. 28(1A):159-64 ( 2008).
McCafferty et al., "Phage Antibodies: Filamentous Phage Displaying Antibody Variable Domains" Nature 348:552-554 (Dec. 1990).
Miao et al., "Hepsin colocalizes with desmosomes and induces progression of ovarian cancer in a mouse model" Int J Cancer 123(9):2041-7 ( 2008).
Milstein and Cuello, "Hybrid hybridomas and their use in immunohistochemistry" Nature 305:537-540 (Oct. 6, 1983).
Moran, P. et al., "Pro-urokinase-type plasminogen activator is a substrate for hepsin" J Biol. Chem. 281(41):30439-30446 (Oct. 13, 2006).
Morimoto and Inouye, "Single-step purification of F(ab')$_2$ fragments of mouse monoclonal antibodies (immunoglobulins G1) by hydrophobic interaction high performance liquid chromatography using TSKgel phenyl-5PW" J. Biochem. Biophys. Meth. 24:107-117 ( 1992).
Morrison et al., "Chimeric human antibody molecules: Mouse antigen-binding domains with human constant region domains" P Natl Acad Sci USA 81(21):6851-6855 (Nov. 1984).
Morrissey et al., "Differential expression of angiogenesis associated genes in prostate cancer bone, liver and lymph node metastases" Clin Exp Metastasis. 25(4):377-88 ( 2008).
Munson and Rodbard, "Ligand: A versatile computerized approach for characterization of ligand-binding systems" Anal. Biochem. 107:220-239 ( 1980).
Netzel-Arnett et al., "Membrane anchored serine proteases: a rapidly expanding group of cell surface proteolytic enzymes with potential roles in cancer" Cancer Metastasis Rev. 22:237-58 (2003).
Neuberger et al., "Recombinant Antibodies Possessing Novel Effector Functions" Nature 312:604-608 (Dec. 13, 1984).
Niculescu-Duvaz and Springer, "Antibody-directed enzyme prodrug therapy (ADEPT): a review" Adv. Drug Deliv. Rev. 26:151-172 ( 1997).
Okigaki et al., "Functional Characterization of Human Hepatocyte Growth Factor Mutants Obtained by Deletion of Structural Domains" Biochemistry 31(40):9555-61 (Oct. 13, 1992).
Presta et al., "Humanization of an antibody directed against IgE" J. Immunol. 151(5):2623-2632 (Sep. 1, 1993).
Presta, "Antibody engineering" Curr. Opin. Struct. Biol. 2:593-596 ( 1992).
Riechmann et al., "Reshaping Human Antibodies for Therapy" Nature 332:323-327 (Mar. 24, 1988).
Rossi, "Making Ribozymes Work in Cells" Curr Biol 4(5):469-71 ( 1994).
Rowland et al., "Drug localisation and growth inhibition studies of vindesine-monoclonal anti-CEA conjugates in a human tumour xenograft" Cancer Immunol. Immunother. 21:183-187 ( 1986).
Schier et al., "Identification of Functional and Structural Amino-Acid Residues by Parsimonious Mutagenesis." Gene 169:147-155 ( 1996).
Schoofs et al., "Epitopes of an influenza viral peptide recognized by antibody at single amino acid resolution" J Immunol 140:611-616 ( 1988).
Shalaby et al., "Development of humanized bispecific antibodies reactive with cytotoxic lymphocytes and tumor cells overexpressing the HER2 protooncogene" J. Exp. Med 175:217-225 (Jan. 1992).
Shia et al., "Conformational lability in serine protease active sites: structures of hepatocyte growth factor activator (HGFA) alone and with the inhibitory domain from HGFA inhibitor-1B" J Mol Biol 346:1335-49 ( 2005).
Shimomura et al., "Hepatocyte Growth Factor Activator Inhibitor, a Novel Kunitz-type Serine Protease Inhibitor" J Biol Chem 272(10):6370-6376 (Mar. 7, 1997).
Shopes, "A Genetically Engineered Human IgG Mutant With Enhanced Cytolytic Activity" J Immunol 148(9):2918-2922 (May 1992).
Sims et al., "A Humanized CD18 Antibody Can Block Function Without Cell Destruction" J Immunol 151(4):2296-2308 (Aug. 15, 1993).
Skeel et al. et al., "Macrophage Stimulating Protein: Purification, Partial Amino Acid Sequence, and Cellular Activity" J Exp Med 173:1227-1234 (May 1991).
Smith, G. P., "Surface presentation of protein epitopes using bacteriophage expression systems" Curr Opin Biotechnol 2(5):668-673 ( 1991).
Stamey et al., "Molecular genetic profiling of Gleason grade 4/5 prostate cancers compared to benign prostatic hyperplasia" J Urol 166(6):2171-2177 (Dec. 2001).
Stephan et al., "Hepsin is highly over expressed in and a new candidate for a prognostic indicator in prostate cancer" J Urol 171(1):187-191 (Jan. 17, 2004).
Stevenson et al., "A Chimeric Antibody With Dual Fc Regions (bisFabFc) Prepared by Manipulations at the IgG Hinge" Anti-Cancer Drug Des 3(4):219-230 ( 1989).
Suresh et al., "Bispecific Monoclonal Antibodies from Hybrid Hybridomas" Method Enzymol. 121:210-228 ( 1986).
Syrigos and Epenetos, "Antibody directed enzyme prodrug therapy (ADEPT): a review of the experimental and clinical considerations" Anticancer Res. 19:605-614 ( 1999).
Tanimoto et al., "Hepsin, a cell surface serine protease identified in hepatoma cells, is overexpressed in ovarian cancer" Cancer Res 57(14):2884-2887 (Jul. 15, 1997).
Torres-Rosado et al., "Hepsin, a putative cell-surface serine protease, is required for mammalian cell growth" Proc Natl Acad Sci U S A. 90(15):7181-5 (Aug. 1, 1993).
Traunecker et al., "Bispecific single chain molecules (Janusins) target cytotoxic lymphocytes on HIV infected cells" EMBO J 10(12):3655-3659 ( 1991).
Tripathi et al., "Laminin-332 is a substrate for hepsin, a protease associated with prostate cancer progression" J Biol Chem. 283(45):30576-84 ( 2008).
Tutt et al., "Trispecific F(ab')$_3$ derivatives that use cooperative signalling via the TCR/CD3 complex and CD2 to activate and redirect resting cytotoxic T cells" J Immunol. 147(1):60-69 (Jul. 1, 1991).
Vaswani and Hamilton et al., "Humanized antibodies as potential therapeutic drugs" Ann. Allergy Asthma Immunol. 1:105-115 ( 1998).
Verhoeyen et al., "Reshaping Human Antibodies: Grafting an Antilysozyme Activity" Science 239:1534-1536 (Mar. 1988).
Wagh et al., "Met-related receptor tyrosine kinase Ron in tumor growth and metastasis" Adv Cancer Res. 100:1-33 ( 2008).
Wahl et al., "Mutation of Cys672 allows recombinant expression of activatible macrophage-stimulating protein" J Biol Chem. 272(24):15053-6 ( 1997).
Wang et al. et al., "Proteolytic Activation of Single-chain Precursor Macrophage-stimulating Protein by Nerve Growth Factor-α and Epidermal Growth Factor-binding Protein, Members of the Kallikrein Family" J Biol Chem 269(19):13806-13810 (May 13, 1994).

(56) References Cited

OTHER PUBLICATIONS

Wang et al. et al., "Proteolytic Conversion of Single Chain Precursor Macrophage-stimulating Protein to a Biologically Active Heterodimer by Contact Enzymes of the Coagulation Cascade" J Biol Chem 269(5):3436-3440 (Feb. 4, 1994).

Wang et al., "Macrophage-stimulating Protein Inhibits Induction of Nitric Oxide Production by Endotoxin- or Cytokine-stimulated Mouse Macrophages" J Biol Chem. 269(19):14027-31 (May 13, 1994).

Wang et al., "Proteolytic cleavage and activation of pro-macrophage-stimulating protein by resident peritoneal macrophage membrane proteases" J Clin Invest. 97(3):720-7 (1996).

Welsh et al., "Analysis of gene expression identifies candidate markers and pharmacological targets in prostate cancer" Cancer Res 61(16):5974-5978 (Aug. 15, 2001).

Wiseman et al., "Ibritumomab tiuxetan radioimmunotherapy for patients with relapsed or refractory non-Hodgkin lymphoma and mild thrombocytopenia: a phase II multicenter trial" Blood 99(12):4336-4342 (2002).

Wiseman et al., "Phase I/II 90Y-Zevalin (yttrium-90 ibritumomab tiuxetan, IDEC-Y2B8) radioimmunotherapy dosimetry results in relapsed or refractory non-Hodgkin's lymphoma" Eur. J Nucl. Med. 27(7):766-777 (Jul. 2000).

Witzig et al., "Randomized Controlled Trial of Yttrium-90—Labeled Ibritumomab Tiuxetan Radioimmunotherapy Versus Rituximab Immunotherapy for Patients With Relapsed or Refractory Low-Grade, Follicular, or Transformed B-Cell Non-Hodgkin's Lymphoma" J Clin. Oncol. 20(10):2453-2463 (May 15, 2002).

Witzig et al., "Treatment with ibritumomab tiuxetan radioimmunotherapy in patients with rituximab-refractory follicular non-Hodgkin's lymphoma" J Clin. Oncol. 20(15):3262-3269 (2002).

Wolff et al., "Monoclonal antibody homodimers: enhanced antitumor activity in nude mice" Cancer Res 53(11):2560-2565 (Jun. 1993).

Wu and Parry, "Hepsin and prostate cancer" Front Biosci. 12:5052-9 (2007).

Wu et al., "Structurall insight into distinct mechanisms of protease inhibition by antibodies" PNAS 104(50):19784-19789 (Dec. 11, 2007).

Xuan et al., "Antibodies neutralizing hepsin protease activity do not impact cell growth but inhibit invasion of prostate and ovarian tumor cells in culture" Cancer Res. 66(7):3611-9 (Apr. 1, 2006).

Yelton et al., "Affinity Maturation of the BR96 Anti-Carcinoma Antibody by Codon-Based Mutagenesis" J Immunol 155:1994-2004 (1995).

Yoshimura et al., "Cloning, Sequencing, and Expression of Human Macrophage Stimulating Protein (MSP,MST1) Confirms MSP as a Member of the Family of Kringle Proteins and Locates the MSP Gene on Chromosome 3" J Biol Chem 268(21):15461-15468 (Jul. 25, 1993).

Zacharski et al., "Expression of the factor VII activating protease, hepsin, in situ in renal cell carcinoma" Thromb Haemostasis 79(4):876-877 (Apr. 1998).

Zhukov et al., "Purification and characterization of hepsin from rat liver microsomes" Biochim Biophys Acta. 1337(1):85-95 (Jan. 4, 1997).

Chevillet et al., "Identification and characterization of small-molecule inhibitors of hepsin" Mol. Cancer Ther. 7:3343-3351 (2008).

Choi et al., "Type II transmembrane serine proteases in cancer and viral infections" Trends in Mol. Med. 15(7):303-312 (2009).

Kataoka et al., "Hepatocyte growth factor activator (HGFA): pathophysiological functions in vivo" The FEBS Journal 277:2230-2237 (2010).

Li et al., "Pegylataed kunitz domain inhibitor suppresses hepsin-mediated invasive tumor growth and metastasis" Cancer Research 69:8395-8402 (2009).

Skeel et al., "Molecular basis of cell and developmental biology: $\alpha_1$-antichymotrypsin is the human plasma inhibitor of macrophage ectoenzymes that cleave pro-macrophage stimulating protein" J. of Biol. Chem. 276:21932-21937 (2001).

Szabo et al., "Type II transmembrane serine proteases in development and disease" Intl. J. of Biochem & Cell Biol. 40:1297-1316 (2008).

MAQKEGGRTVPCCSRPKVAALTAGTLLLLTAIGAASWAIVAVLLRSDQEPLYPVQVSSAD
ARLMVFDKTEGTWRLLCSSRSNARVAGLSCEEMGFLRALTHSELDVRTAGANGTSGFFCV
DEGRLPHTQRLLEVISVCDCPRGRFLAAICQDCGRRKLPVDRIVGGRDTSLGRWPWQVSL
RYDGAHLCGGSLLSGDWVLTAAHCFPERNRVLSRWRVFAGAVAQASPHGLQLGVQAVVYH
GGYLPFRDPNSEENSNDIALVHLSSPLPLTEYIQPVCLPAAGQALVDGKICTVTGWGNTQ
YYGQQAGVLQEARVPIISNDVCNGADFYGNQIKPKMFCAGYPEGGIDACQGDSGGPFVCE
DSISRTPRWRLCGIVSWGTGCALAQKPGVYTKVSDFREWIFQAIKTHSEASGMVTQL
(SEQ ID NO:18)

*FIG. 8*

Met Ala Gln Lys Glu Gly Gly Arg Thr Val Pro Cys Cys Ser Arg Pro
1               5                   10                  15
Lys Val Ala Ala Leu Thr Ala Gly Thr Leu Leu Leu Leu Thr Ala Ile
                20                  25                  30
Gly Ala Ala Ser Trp Ala Ile Val Ala Val Leu Leu Arg Ser Asp Gln
                35                  40                  45
Glu Pro Leu Tyr Pro Val Gln Val Ser Ser Ala Asp Ala Arg Leu Met
        50                  55                  60
Val Phe Asp Lys Thr Glu Gly Thr Trp Arg Leu Leu Cys Ser Ser Arg
65                  70                  75                  80
Ser Asn Ala Arg Val Ala Gly Leu Ser Cys Glu Glu Met Gly Phe Leu
                85                  90                  95
Arg Ala Leu Thr His Ser Glu Leu Asp Val Arg Thr Ala Gly Ala Asn
                100                 105                 110
Gly Thr Ser Gly Phe Phe Cys Val Asp Glu Gly Arg Leu Pro His Thr
                115                 120                 125
Gln Arg Leu Leu Glu Val Ile Ser Val Cys Asp Cys Pro Arg Gly Arg
                130                 135                 140
Phe Leu Ala Ala Ile Cys Gln Gly Glu Ile Leu Lys Leu Arg Thr Leu
145                 150                 155                 160
Ser Phe Arg Pro Leu Gly Arg Pro Arg Pro Leu Lys Leu Pro Arg Met
                165                 170                 175
Gly Pro Cys Thr Phe Arg Pro Pro Arg Ala Gly Pro Ser Leu Gly Ser
                180                 185                 190
Gly Asp Leu Gly Ser Ser Pro Leu Ser Pro Pro Pro Ala Asp Pro Cys
                195                 200                 205
Pro Thr Asp Cys Gly Arg Arg Lys Leu Pro Val Asp Arg Ile Val Gly
        210                 215                 220
Gly Arg Asp Thr Ser Leu Gly Arg Trp Pro Trp Gln Val Ser Leu Arg
225                 230                 235                 240

*FIG. 9A*

```
Try Asp Gly Ala His Leu Cys Gly Gly Ser Leu Leu Ser Gly Asp Trp
                245                 250                 255
Val Leu Thr Ala Ala His Cys Phe Pro Glu Arg Asn Arg Val Leu Ser
                260                 265                 270
Arg Trp Arg Val Phe Ala Gly Ala Val Ala Gln Ala Ser Pro His Gly
            275                 280                 285
Leu Gln Leu Gly Val Gln Ala Val Val Tyr His Gly Gly Tyr Leu Pro
            290                 295                 300
Phe Arg Asp Pro Asn Ser Glu Glu Asn Ser Asn Asp Ile Ala Leu Val
305                 310                 315                 320
His Leu Ser Ser Pro Leu Pro Leu Thr Glu Tyr Ile Gln Pro Val Cys
                325                 330                 335
Leu Pro Ala Ala Gly Gln Ala Leu Val Asp Gly Lys Ile Cys Thr Val
                340                 345                 350
Thr Gly Trp Gly Asn Thr Gln Tyr Tyr Gly Gln Gln Ala Gly Val Leu
            355                 360                 365
Gln Glu Ala Arg Val Pro Ile Ile Ser Asn Asp Val Cys Asn Gly Ala
            370                 375                 380
Asp Phe Tyr Gly Asn Gln Ile Lys Pro Lys Met Phe Cys Ala Gly Tyr
385                 390                 395                 400
Pro Glu Gly Gly Ile Asp Ala Cys Gln Gly Asp Ser Gly Gly Pro Phe
                405                 410                 415
Val Cys Glu Asp Ser Ile Ser Arg Thr Pro Arg Trp Arg Leu Cys Gly
                420                 425                 430
Ile Val Ser Trp Gly Thr Gly Cys Ala Leu Ala Gln Lys Pro Gly Val
            435                 440                 445
Tyr Thr Lys Val Ser Asp Phe Arg Glu Trp Ile Phe Gln Ala Ile Lys
            450                 455                 460
Thr His Ser Glu Ala Ser Gly Met Val Thr Gln Leu
465                 470                 475

(SEQ ID NO:19)
```

*FIG. 9B*

```
MGWLPLLLLL TQCLGVPGQR SPLNDFQVLR GTELQHLLHA VVPGPWQEDV ADAEECAGRC
GPLMDCRAFH YNVSSHGCQL LPWTQHSPHT RLRRSGRCDL FQKKDYVRTC IMNNGVGYRG
TMATTVGGLP CQAWSHKFPN DHKYTPTLRN GLEENFCRNP DGDPGGPWCY TTDPAVRFQS
CGIKSCREAA CVWCNGEEYR GAVDRTESGR ECQRWDLQHP HQHPFEPGKF LDQGLDDNYC
RNPDGSERPW CYTTDPQIER EFCDLPRCGS EAQPRQEATT VSCFRGKGEG YRGTANTTTA
GVPCQRWDAQ IPHQHRFTPE KYACKDLREN FCRNPDGSEA PWCFTLRPGM RAAFCYQIRR
CTDDVRPQDC YHGAGEQYRG TVSKTRKGVQ CQRWSAETPH KPQFTFTSEP HAQLEENFCR
NPDGDSHGPW CYTMDPRTPF DYCALRRCAD DQPPSILDPP DQVQFEKCGK RVDRLDQRRS
KLRVVGGHPG NSPWTVSLRN RQGQHFCGGS LVKEQWILTA RQCFSSCHMP LTGYEVWLGT
LFQNPQHGEP SLQRVPVAKM VCGPSGSQLV LLKLERSVTL NQRVALICLP PEWYVVPPGT
KCEIAGWGET KGTGNDTVLN VALLNVISNQ ECNIKHRGRV RESEMCTEGL LAPVGACEGD
YGGPLACFTH NCWVLEGIII PNRVCARSRW PAVFTRVSVF VDWIHKVMRL G
```

(SEQ ID NO:20)

FIG. 10

METHODS AND COMPOSITIONS FOR MODULATING HEPSIN ACTIVATION OF MACROPHAGE-STIMULATING PROTEIN

CROSS-REFERENCE TO RELATED APPLICATIONS

This application is a national stage entry of International Application No. PCT/US2010/05360 having an international filing date of Oct. 21, 2012, which claims the benefit of U.S. Provisional Patent Application No. 61/253,990 filed Oct. 22, 2009, the contents of which is incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 23, 2012, is named P4379R1.txt and is 19,764 bytes in size.

FIELD OF THE INVENTION

The present invention relates generally to the fields of molecular biology and growth factor regulation. More specifically, the invention concerns modulators of enzymatic activation of macrophage-stimulating protein, and uses of said modulators.

BACKGROUND OF THE INVENTION

Macrophage-stimulating protein (MSP) mediates its biological activities via binding and activation of the receptor tyrosine kinase Ron, a member of the Met-proto-oncogene family (Leonard & Danilkovitch, 2000). Interaction of MSP with its receptor leads to receptor phosphorylation and kinase activation. The MSP/Ron pathway has been implicated in tumorigenesis of various cancers (see, e.g., Wagh et al., 2008). MSP is a plasma protein which is constitutively synthesized in hepatic parenchymal cells primarily, but it is also expressed in lung, adrenal gland and placenta in low levels. MSP circulates in blood as an inactive single-chain precursor (pro-MSP), which requires proteolytic cleavage at the Ser-Lys-Leu-Arg483↓Val484 (SEQ ID NO:1) bond to attain functional activity (Skeel et al., 1991) (Yoshimura et al., 1993). Active MSP is a heterodimer of α- and the β-subunits held together by a disulfide bond. MSP was known to be activated at the extravascular site by several trypsin-like serine proteases (Bhatt et al., 2007; Kawaguchi et al., 2009; Wang et al., 1994b; Wang et al., 1996; Wang et al., 1994c).

Hepsin is a member of the type II transmembrane serine protease family (Netzel-Arnett et al., 2003; Wu & Parry, 2007) and was identified as one of the most highly upregulated genes in prostate cancer (Dhanasekaran et al., 2001; Luo et al., 2001; Magee et al., 2001; Stamey et al., 2001; Stephan et al., 2004; Welsh et al., 2001) Immunohistochemical staining revealed strong expression in late stage tumors and metastatic bone lesions (Morrissey et al., 2008; Xuan et al., 2006) suggesting a role of hepsin in tumor progression. Moreover, based on gene expression analysis hepsin has also been implicated in ovarian cancer (Tanimoto et al., 1997), renal cell carcinoma (Betsunoh et al., 2007; Zacharski et al., 1998) and endometrial cancer (Matsuo et al., 2008). Beliveau et al stated that hepsin does not cleave pro-MSP (Beliveau et al., (2009) FEBS J. 276:2213-26).

There is a clear need for a comprehensive understanding of hepsin's physiological substrates. The invention fulfills this need and provides other benefits.

All references cited herein, including patent applications and publications, are incorporated by reference in their entirety.

SUMMARY OF THE INVENTION

It is disclosed herein that hepsin efficiently converts pro-macrophage-stimulating protein (pro-MSP) into macrophage-stimulating protein (MSP) by cleavage at the $Arg_{483}$-$Val_{484}$ peptide bond. As described herein, a physiological substrate for hepsin is pro-macrophage stimulating protein, which is a ligand of the receptor tyrosine kinase Ron, a member of the Met-proto-oncogene family. Hepsin is shown herein to cleave pro-MSP with potent activity, resulting in activated MSP that exhibits normal biological activities. The invention provides methods and compositions based at least in part on these findings, which are described in detail herein. Hepsin and its interaction with pro-MSP is a unique and advantageous target for greater fine-tuning in designing prophylactic and/or therapeutic approaches against pathological conditions associated with abnormal or unwanted hepsin and/or MSP/Ron-mediated biological activity. Thus, the invention provides methods, compositions, kits and articles of manufacture for identifying and for using substances that are capable of modulating the hepsin and/or MSP/Ron-mediated biological pathway through modulation of molecular interactions involved in the regulation of MSP activation.

Accordingly, in one aspect, the invention provides a method of screening for (or identifying) a candidate inhibitor (i.e., antagonist) substance that inhibits hepsin activation of pro-MSP, said method comprising: (a) contacting a candidate substance with a first sample comprising hepsin and a pro-MSP substrate, and (b) comparing amount of pro-MSP activation in the sample with amount of pro-MSP activation in a reference sample comprising similar amounts of hepsin and pro-MSP substrate as the first sample but that has not been contacted with said candidate substance, whereby a decrease in amount of pro-MSP activation in the first sample compared to the reference sample indicates that the candidate substance is capable of inhibiting hepsin activation of pro-MSP. In one embodiment, hepsin in a sample is in an effective amount for activating said pro-MSP substrate. A pro-MSP substrate suitable for use in these methods can be in a number of forms, so long as it mimics the characteristic of the hepsin cleavage site on pro-MSP.

Examples of pro-MSP substrate include, but are not limited to, full length single chain MSP comprising a wild type form of the $Arg_{483}$-$Val_{484}$ peptide bond, and any fragment of MSP that comprises this peptide linkage. Such fragment can be any length, for example at least (about) 5, 7, 10, 15, 20, 25 amino acids in length, or between (about) 4 and 25, 5 and 20, 7 and 15 amino acids in length. Generally and preferably, a pro-MSP substrate comprises an $Arg_{483}$-$Val_{484}$ peptide bond capable of being cleaved by wild type hepsin. In some embodiments, the pro-MSP substrate is a synthetic pro-MSP substrate.

In another aspect, the invention provides a method of screening for a substance that blocks pro-MSP activation by hepsin, said method comprising screening for a substance that binds (preferably, but not necessarily, specifically) hepsin or pro-MSP and blocks specific interaction (e.g., binding) between hepsin and pro-MSP. In some embodiments, the substance competes with hepsin for binding to MSP. In some embodiments, the substance competes with pro-MSP for binding to hepsin. In one embodiment, the substance comprises, consists or consists essentially of an amino acid sequence having at least about 60%, 70%, 80%, 90%, 95%, 99% sequence similarity or identity with respect to pro-MSP (e.g., human), e.g., a fragment of human MSP comprising amino acid residues $Arg_{483}$ peptide linked to $Val_{484}$. In some embodiments wherein the substance comprises, consists or consists essentially of such an amino acid sequence, the fragment is mutated or devoid of at least a portion of the MSP sequence associated with activity, e.g. activation of Ron.

As would be evident to one skilled in the art, screening assays consistent with those described above can also comprise a first step of screening for formation of hepsin-MSP complex to obtain a first set of candidate modulatory substance, followed by a second step of screening based on ability of the first set of candidate modulatory substance to modulate activation of pro-MSP and/or conversion of pro-MSP into a form that is biologically active. Suitable readouts can be any that would be evident to one skilled in the art, based on knowledge of enzyme-substrate complex formation and/or biological activities associated with the hepsin/MSP/Ron signaling pathway. Enzyme-substrate complex formation can be measured using, for example, routine biochemical assays (e.g., gel electrophoresis, chromatography, NMR, etc.).

In one aspect, the invention provides antagonists that disrupt the hepsin/MSP interaction. For example, the invention provides a molecule that inhibits hepsin cleavage of pro-MSP (e.g., cleavage at the $Arg_{483}$-$Val_{484}$ position). The molecule can exert its inhibitory function in any number of ways, including but not limited to binding to either hepsin or pro-MSP such that hepsin cleavage of pro-MSP is inhibited, binding to hepsin-pro-MSP complex such that cleavage of pro-MSP is inhibited, and/or binding to pro-MSP or hepsin (singly or in complex) such that effects of MSP cleavage by hepsin is inhibited (e.g., inhibition of release of MSP subsequent to cleavage by hepsin). In one embodiment, an antagonist molecule of the invention inhibits biological activities associated with pro-MSP/Ron activation.

In one aspect, an antagonist of the invention is derived from the discovery described herein that a fragment from hepatocyte growth factor activator inhibitors (HAI-1, HAI-1B, HAI-2) is a potent inhibitor of hepsin activation of pro-MSP. In one embodiment, the invention provides an antagonist of pro-MSP activation by hepsin, said antagonist comprising at least a portion (including all) of human HAI-1, HAI-1B or HAI-2. In one embodiment, said portion comprises a Kunitz domain (KD) sequence capable of inhibiting pro-MSP activation by hepsin. In one embodiment, said Kunitz domain sequence is Kunitz domain 1 (KD1) of HAI-1 or HAI-1B. In one embodiment, an antagonist of the invention comprises a variant KD1 sequence having at least about 70%, 75%, 80%, 85%, 90%, 95%, 97%, 98%, 99% sequence identity with wild type KD1 of human HAI-1, wherein said variant sequence has at least comparable ability as wild type KD1 in inhibiting hepsin cleavage of human pro-MSP. In one embodiment, an antagonist of the invention comprises a variant KD1 sequence having between about 70% and 99%, about 75% and 98%, about 80% and 97%, 85% and 95% sequence identity with wild type KD1 of human HAI-1, wherein said sequence has at least comparable ability as wild type KD1 in inhibiting hepsin cleavage of human pro-MSP. In one embodiment, said Kunitz domain sequence is one or both of the Kunitz domains of HAI-2. In one embodiment, an antagonist of the invention comprises a variant HAI-2 Kunitz domain sequence having at least about 70%, 75%, 80%, 85%, 90%, 95%, 97%, 98%, 99% sequence identity with the corresponding Kunitz domain(s) of wild type human HAI-2, wherein said variant sequence has at least comparable ability as wild type HAI-2 in inhibiting hepsin cleavage of human pro-MSP. In one embodiment, an antagonist of the invention comprises a variant HAI-2 Kunitz domain sequence having between about 70% and 99%, about 75% and 98%, about 80% and 97%, 85% and 95% sequence identity with the corresponding Kunitz domain(s) of wild type human HAI-2, wherein said sequence has at least comparable ability as wild type HAI-2 in inhibiting hepsin cleavage of human pro-MSP.

In some embodiments, an antagonist of the invention is or comprises a small molecule, peptide, antibody, antibody fragment, aptamer, or a combination thereof. Antagonists as described herein can be routinely obtained using techniques known in the art (including those described in greater detail below) based on the discovery of the interaction of hepsin and pro-MSP as described herein. For example, in some embodiments, an antagonist of the invention competes with hepsin for binding to pro-MSP, but does not have ability to cleave pro-MSP at the hepsin cleavage site (e.g., at $Arg_{483}$-$Val_{484}$). In some embodiments, an antagonist of the invention competes with pro-MSP for binding to hepsin. For example, in one embodiment, said antagonist comprises, consists or consists essentially of an amino acid sequence having at least about 60%, 70%, 80%, 90%, 95%, 98%, 99% sequence similarity or identity with respect to pro-MSP (e.g., human pro-MSP) and is capable of substantially binding hepsin, but lacks a hepsin cleavage site (e.g., pro-MSP $Arg_{483}$-$Val_{484}$ peptide link) and/or lacks biological activity (e.g., wherein the MSP β chain is mutated such that its function is substantially reduced or eliminated, etc.). In one embodiment, an antagonist of the invention comprises, consists or consists essentially of a pro-MSP fragment capable of binding hepsin, wherein said fragment is devoid of at least a portion of a MSP sequence associated with biological activity.

Thus, the invention provides a MSP (or pro-MSP) mutant capable of substantially binding hepsin but has decreased MSP biological activity compared to wild type MSP, e.g. an antagonist of MSP activity or a MSP variant exhibiting a reduction, but not an absence, of MSP biological activity. In one embodiment, an antagonist of the invention is capable of inhibiting the biological activity of wild type (in vitro or in vivo) MSP (such biological activity includes but is not limited to biological activity with respect to plasminogen as a substrate). In one embodiment, an antagonist of the invention provides reduced MSP biological activity.

In some embodiments, an antibody antagonist of the invention comprises an anti-hepsin antibody that blocks hepsin activation of pro-MSP. In some embodiments, the anti-hepsin antibody comprises (a) a light chain comprising (i) HVR-L1 comprising sequence RASQSVSSAVA (SEQ ID NO:2); (ii) HVR-L2 comprising sequence SASSLYS (SEQ ID NO:3); and (iii) HVR-L3 comprising sequence QQYYSSYYLLT (SEQ ID NO:4); and/or (b) a heavy chain comprising (i) HVR-H1 comprising sequence GFNFSYSYMH (SEQ ID NO:5); (ii) HVR-H2 comprising sequence ASIYSYYG-STYYADSVKG (SEQ ID NO:6); and (iii) HVR-H3 comprising sequence ARSDSWSYKSGYTQKIYSKGLDY (SEQ ID NO:7). In some embodiments, the anti-hepsin antibody comprises a light chain variable region comprising sequence DIQMTQSPSSLSASVGDRVTITCRASQS-VSSAVAWYQQKPGKAPKLLIYSASSLYSGVPSRFS GSRSGTDFTLTISSLQPEDFATYYC-QQYYSSYYLLTFGQGTKVEIK (SEQ ID NO:8) and/or a heavy chain variable region comprising sequence EVQLVESGGGLVQPGGSLRLSCAASGFN-FSYSYMHWVRQAPGKGLEWVASIYSYYGSTYYA DSVKGRFTISADTSKNTAYLQMNSL-RAEDTAVYYCARSDSWSYKS-GYTQKIYSKGLDYWGQ GTLVTVSS (SEQ ID NO:9). In some embodiments, the antibody is a monoclonal antibody. In other embodiments, the antibody is a polyclonal antibody. In some embodiments, the antibody is selected from the group consisting of a chimeric antibody, an affinity matured antibody, a humanized antibody, and a human antibody. In certain embodiments, the antibody is an antibody fragment. In some embodiments, the antibody is a Fab, Fab', Fab'-SH, F(ab')$_2$, or scFv.

In some embodiments, binding of a substance or molecule of the invention to hepsin inhibits hepsin activation of hepsin substrate. In some embodiments, binding or the substance or molecule of the invention to hepsin competitively inhibits hepsin activation of hepsin substrate. In one embodiment, the substance binds hepsin in the absence of a compound that blocks hepsin active (e.g., catalytic) site, but does not bind hepsin in the presence of the compound that blocks hepsin active site.

In some embodiments, binding of said substance or molecule to hepsin inhibits cell growth (such as cell proliferation, survival, angiogenesis, morphogenesis, migration) induced by MSP. In some embodiments, binding of said substance or molecule to hepsin inhibits Ron receptor activation. In some embodiments, binding of a substance or molecule of the invention to hepsin inhibits hepsin substrate binding to hepsin. In some embodiments, binding of a substance or molecule of the invention to hepsin does not inhibit substrate binding to hepsin. In some embodiments, binding of a substance or molecule of the invention to hepsin inhibits hepsin activity, such as hepsin enzymatic activity. In some embodiments, hepsin enzymatic activity comprises cleavage of polypeptide substrate of hepsin. In one embodiment, the polypeptide substrate of hepsin is pro-MSP.

In some embodiments, an antagonist of the invention is obtained by a screening or identification method of the invention as described herein.

In one aspect, an antagonist molecule of the invention is linked to a toxin such as a cytotoxic agent. These molecules can be formulated or administered in combination with an additive/enhancing agent, such as a radiation and/or chemotherapeutic agent.

The invention also provides methods and compositions useful for modulating disease states associated with dysregulation of the hepsin/MSP/Ron axis. Thus, in one aspect, the invention provides a method of modulating pro-MSP activation in a subject, said method comprising administering to the subject a hepsin/MSP modulator molecule of the invention (e.g., an antagonist molecule, as described herein, that inhibits hepsin cleavage of pro-MSP), whereby pro-MSP activation is modulated. In one embodiment, said molecule is an antagonist that inhibits MSP activity. In one aspect, the invention provides a method of treating a pathological condition associated with dysregulation of MSP in a subject, said method comprising administering to the subject an antagonist of the invention (e.g., any of the antagonists of pro-MSP cleavage by hepsin as described herein), whereby pro-MSP activation is inhibited. In one aspect, the invention provides a method of modulating Ron activation in a subject, said method comprising administering to the subject an MSP/Ron modulator molecule of the invention (e.g., an antagonist molecule, as described herein, that inhibits hepsin cleavage of pro-MSP), whereby Ron activation is modulated. In one embodiment, said molecule is an MSP/Ron antagonist that inhibits MSP/Ron activity. In one aspect, the invention provides a method of treating a pathological condition associated with dysregulation of Ron in a subject, said method comprising administering to the subject a Ron antagonist of the invention (e.g., any of the antagonists of pro-MSP cleavage by hepsin as described herein), whereby Ron activation is inhibited.

The MSP/Ron signaling pathway is involved in multiple biological and physiological functions, including, e.g., cell growth stimulation (e.g. cell proliferation, cell survival, cell migration, cell morphogenesis) and immune response (e.g., increased inflammatory response, increased NO production by macrophages).

Thus, in one aspect, the invention provides a method of inhibiting the growth (e.g., cell growth, proliferation or survival) of a cell that expresses Ron or MSP or both, wherein growth of the cell is at least in part dependent upon hepsin, Ron and/or MSP, said method comprising contacting said cell with an antagonist of the invention thereby causing an inhibition of growth of said cell.

In one aspect, the invention provides a method for inhibiting the migration of a cell, wherein migration of said cell is at least in part dependent upon hepsin, Ron and/or MSP, said method comprising contacting said cell with an effective amount of an antagonist of the invention, thereby inhibiting the growth of said cell.

Thus, in one aspect, the invention provides a method of promoting apoptosis of a cell that expresses Ron or MSP or both, wherein survival of the cell is at least in part dependent upon hepsin, Ron and/or MSP, said method comprising contacting said cell with an antagonist of the invention thereby causing an inhibition of growth of said cell.

In yet another aspect, the invention provides a method of inhibiting an immune response (e.g., inflammation), wherein the immune response is at least in part dependent upon hepsin, Ron and/or MSP, said method comprising administering to a cell, tissue, and/or subject with a condition associated with abnormal immune response an antagonist of the invention, whereby an immune response is inhibited.

In one aspect, the invention provides use of an antagonist of the invention in the preparation of a medicament for the therapeutic and/or prophylactic treatment of a disease, such as a cancer, a tumor, a cell proliferative disorder, and/or an immune (such as autoimmune) disorder. The antagonist can be of any form described herein, including antibody, antibody fragment, small molecule (e.g., an organic molecule), polypeptide (e.g., an oligopeptide), nucleic acid (e.g., an oligonucleotide, such as an antisense oligonucleotide or interfering RNA), an aptamer, or combination thereof.

In one aspect, the invention provides use of a nucleic acid of the invention in the preparation of a medicament for the therapeutic and/or prophylactic treatment of a disease, such as a cancer, a tumor, a cell proliferative disorder and/or an immune (such as autoimmune) disorder.

In one aspect, the invention provides use of an expression vector of the invention in the preparation of a medicament for the therapeutic and/or prophylactic treatment of a disease, such as a cancer, a tumor, a cell proliferative disorder and/or an immune (such as autoimmune) disorder.

In one aspect, the invention provides use of a host cell of the invention in the preparation of a medicament for the therapeutic and/or prophylactic treatment of a disease, such as a cancer, a tumor, a cell proliferative disorder and/or an immune (such as autoimmune) disorder.

In one aspect, the invention provides use of an article of manufacture of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder (wound healing).

In one aspect, the invention provides use of a kit of the invention in the preparation of a medicament for the therapeutic and/or prophylactic treatment of a disease, such as a cancer, a tumor, a cell proliferative disorder and/or an immune (such as autoimmune) disorder).

Methods of the invention can be used to affect any suitable pathological state, for example, cells and/or tissues associated with dysregulation of the hepsin and/or Ron/MSP signaling pathway. Exemplary disorders are described herein, and include a cancer selected from the group consisting of non-small cell lung cancer, ovarian cancer, thyroid cancer, testicular cancer, endometrial cancer, head and neck cancer (e.g., head and neck squamous cell carcinoma), brain cancer (e.g., neuroblastoma or meningioma), skin cancer (e.g., melanoma, basal cell carcinoma, or squamous cell carcinoma), bladder cancer (e.g., transitional cell carcinoma), breast carcinoma, gastric cancer, colorectal cancer (CRC), hepatocellular carcinoma, cervical cancer, lung cancer, pancreatic cancer, prostate cancer, and renal cancer, and endometrial cancer.

In one embodiment, a cell that is targeted in a method of the invention is a cancer cell. For example, a cancer cell can be one selected from the group consisting of a breast cancer cell, a colorectal cancer cell, a lung cancer cell (e.g., a non-small cell lung cancer cell), a thyroid cancer cell, a multiple myeloma cell, a testicular cancer cell, a papillary carcinoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell (e.g., a transitional cell carcinoma cell), a gastric carcinoma cell, a head and neck squamous carcinoma cell, a melanoma cell, a leukemia cell, an endometrial cancer cell, and a colon adenoma cell. In one embodiment, a cell that is targeted in a method of the invention is a hyperproliferative and/or hyperplastic cell. In another embodiment, a cell that is targeted in a method of the invention is a dysplastic cell. In yet another embodiment, a cell that is targeted in a method of the invention is a metastatic cell.

Methods of the invention can further comprise additional treatment steps. For example, in one embodiment, a method further comprises a step wherein a targeted cell and/or tissue (e.g., a cancer cell) is exposed to radiation treatment or a chemotherapeutic agent.

As described herein, Ron activation is an important biological process the dysregulation of which leads to numerous pathological conditions. Accordingly, in one embodiment of methods of the invention, a cell that is targeted (e.g., a cancer cell) is one in which activation of Ron is enhanced as compared to a normal cell of the same tissue origin. In one embodiment, a method of the invention causes the death of a targeted cell. For example, contact with an antagonist of the invention may result in a cell's inability to signal through the Ron pathway.

Dysregulation of Ron activation (and thus signaling) can result from a number of cellular changes, including, for example, overexpression of MSP (Ron's cognate ligand) and/or Ron itself. Accordingly, in some embodiments, a method of the invention comprises targeting a cell wherein Ron or MSP, or both, is more abundantly expressed by said cell (e.g., a cancer cell) as compared to a normal cell of the same tissue origin.

Dysregulation of pro-MSP activation (and thus activation of Ron) can result from a number of cellular changes, including, for example, overexpression of hepsin, pro-MSP, and/or Ron. Accordingly, in some embodiments, a method of the invention comprises targeting a cell or tissue wherein hepsin, pro-MSP and/or Ron, is more abundantly expressed by said cell or tissue (e.g., a cancer cell or tissue) as compared to a normal corresponding cell or tissue.

In one aspect, the invention provides compositions comprising one or more antagonists of the invention and a carrier. In one embodiment, the carrier is pharmaceutically acceptable.

In one aspect, the invention provides nucleic acids encoding an antagonist of the invention. In one embodiment, a nucleic acid of the invention encodes an antagonist which is or comprises a polypeptide (e.g., an oligopeptide). In one embodiment, a nucleic acid of the invention encodes an antagonist which is or comprises an antibody or fragment thereof.

In one aspect, the invention provides vectors comprising a nucleic acid of the invention.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods for making an antagonist of the invention. For example, the invention provides a method of making an antagonist which is or comprises an antibody (or fragment thereof), said method comprising expressing in a suitable host cell a recombinant vector of the invention that comprises a sequence encoding said antibody (or fragment thereof), and recovering said antibody (or fragment thereof). In another example, the invention provides a method of making an antagonist which is or comprises a polypeptide (such as an oligopeptide), said method comprising expressing in a suitable host cell a recombinant vector of the invention encoding said polypeptide (such as an oligopeptide), and recovering said polypeptide (such as an oligopeptide).

In one aspect, the invention provides an article of manufacture comprising a container; and a composition contained within the container, wherein the composition comprises one or more antagonists of the invention. In one embodiment, the composition comprises a nucleic acid of the invention. In one embodiment, a composition comprising an antagonist further comprises a carrier, which in some embodiments is pharmaceutically acceptable. In one embodiment, an article of manufacture of the invention further comprises instructions for administering the composition (e.g., the antagonist) to a subject.

In one aspect, the invention provides a kit comprising a first container comprising a composition comprising one or more antagonists of the invention; and a second container comprising a buffer. In one embodiment, the buffer is pharmaceutically acceptable. In one embodiment, a composition comprising an antagonist further comprises a carrier, which in some embodiments is pharmaceutically acceptable. In one embodiment, a kit further comprises instructions for administering the composition (e.g., the antagonist) to a subject.

In one aspect, the invention provides a composition comprising purified pro-MSP and hepsin. In some embodiments, the composition further comprises a cell expressing Ron.

In one aspect, the invention provides methods for detecting pro-MSP in a sample comprising (1) contacting the sample with hepsin under conditions permitting hepsin proteolytic processing of MSP and (2) detecting presence of hepsin activated MSP.

In one aspect, the invention provides methods for detecting hepsin in a sample comprising (1) contacting the sample with pro-MSP under conditions permitting hepsin proteolytic processing of MSP and (2) detecting presence of hepsin activated MSP.

BRIEF DESCRIPTION OF THE DRAWINGS

FIG. 1 discloses SEQ ID NO:17.

FIG. 8: One embodiment of an amino acid sequence of native human hepsin (SEQ ID NO: 18).

FIG. 9: (A) & (B) Another embodiment of an amino acid sequence of native human hepsin (SEQ ID NO: 19).

FIG. 10: One embodiment of an amino acid sequence of native human pro-macrophage-stimulating protein (pro-MSP) (SEQ ID NO: 20).

DETAILED DESCRIPTION OF THE INVENTION

Figure 1:
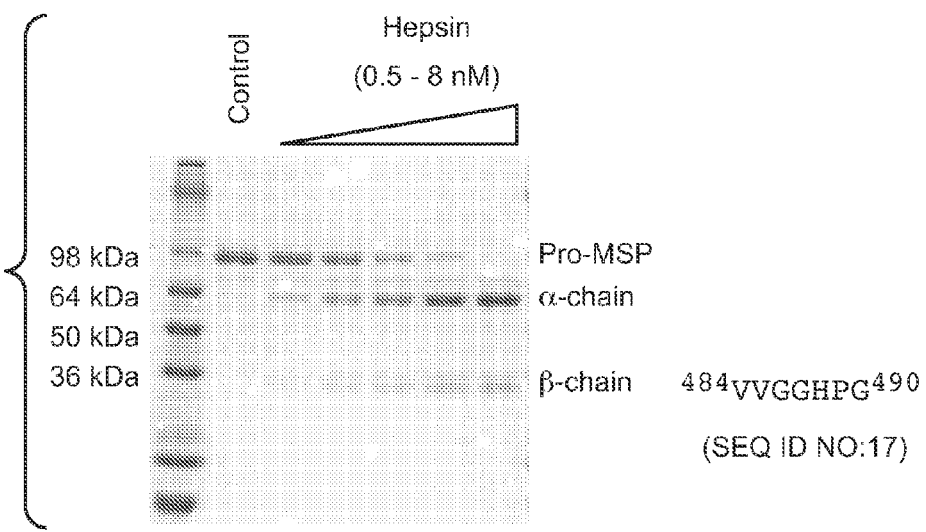
FIG. 1: In vitro activation of pro-MSP by hepsin. Recombinant hepsin activated pro-MSP in a dose dependent manner upon incubation for 1 hour at 37° C. The products were separated on an SDS-PAGE under reducing condition. The N-terminal sequencing of the ~25 kDa band (depicted) indicated that this was the β-chain and thus hepsin cleaved pro-MSP at the $Arg_{483}$-$Val_{484}$ bond.

The invention provides methods, compositions, kits and articles of manufacture comprising modulators of the MSP/Ron signaling pathway, including methods of using such modulators.

Details of these methods, compositions, kits and articles of manufacture are provided herein.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

Definitions

The term "hepsin" as used herein encompasses native sequence polypeptides, polypeptide variants and fragments of a native sequence polypeptide and polypeptide variants (which are further defined herein) that is capable of pro-MSP cleavage in a manner similar to wild type hepsin. The hepsin polypeptide described herein may be that which is isolated from a variety of sources, such as from human tissue types or from another source, or prepared by recombinant or synthetic methods. The terms "hepsin", "hepsin polypeptide", "hepsin enzyme", and "hepsin protein" also include variants of a hepsin polypeptide as disclosed herein.

A "native sequence hepsin polypeptide" comprises a polypeptide having the same amino acid sequence as the corresponding hepsin polypeptide derived from nature. In one embodiment, a native sequence hepsin polypeptide comprises the amino acid sequence of FIG. 8. In one embodiment, a native sequence hepsin polypeptide comprises the amino acid sequence of FIG. 9. Such native sequence hepsin polypeptide can be isolated from nature or can be produced by recombinant or synthetic means. The term "native sequence hepsin polypeptide" specifically encompasses naturally-occurring truncated or secreted forms of the specific hepsin polypeptide (e.g., an extracellular domain sequence), naturally-occurring variant forms (e.g., alternatively spliced forms) and naturally-occurring allelic variants of the polypeptide.

"Hepsin polypeptide variant", or variations thereof, means a hepsin polypeptide, generally an active hepsin polypeptide, as defined herein having at least about 80% amino acid sequence identity with any of the native sequence hepsin polypeptide sequences as disclosed herein. Such hepsin polypeptide variants include, for instance, hepsin polypeptides wherein one or more amino acid residues are added, or deleted, at the N- or C-terminus of a native amino acid sequence. Ordinarily, a hepsin polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence hepsin polypeptide sequence as disclosed herein. Ordinarily, hepsin variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, hepsin variant polypeptides will have no more than one conservative amino acid substitution as compared to a native hepsin polypeptide sequence, alternatively no more than 2, 3, 4, 5, 6, 7, 8, 9, or 10 conservative amino acid substitution as compared to the native hepsin polypeptide sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, as described in U.S. Pat. No. 6,828,146.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "macrophage-stimulating protein" and "MSP", or "pro-macrophage-stimulating protein" and "pro-MSP", as used herein, refers, unless specifically or contextually indicated otherwise, to any native or variant (whether naturally occurring or synthetic) MSP polypeptide that is capable of, or a MSP polypeptide that can be activated by hepsin into activated MSP that is capable of, activating plasminogen under conditions that permit such process to occur. The term "wild type MSP" generally refers to a polypeptide comprising the amino acid sequence of a naturally occurring MSP protein, for example as set forth in FIG. 10 and listed at SwissProt Accession No. P26927 (the references listed at this accession number are incorporated herein by reference).

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population comprise essentially identical amino acid sequence except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al., *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with a composition or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and other angiogenesis-related disorders.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation and/or invasiveness. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, compositions and/or methods of the invention are used to delay development of a disease or disorder.

An "effective amount" refers to an amount effective, at dosages and for periods of time necessary, to achieve the desired therapeutic or prophylactic result.

A "therapeutically effective amount" of a molecule (e.g., antagonist) of the invention may vary according to factors such as the disease state, age, sex, and weight of the individual, and the ability of the molecule (e.g., antagonist) to elicit a desired response in the individual. A therapeutically effective amount is also one in which any toxic or detrimental effects of the molecule (e.g., antagonist) are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem Intl. Ed. Engl.*, 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl)benzenesulfonamide; and pharmaceutically acceptable salts, acids or derivatives of any of the above.

A "growth inhibitory agent" when used herein refers to a compound or composition which inhibits growth of a cell whose growth is dependent upon MSP activation either in vitro or in vivo. Thus, the growth inhibitory agent may be one which significantly reduces the percentage of MSP-dependent cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

Compositions and Methods of the Invention

A. Antibodies

In one embodiment, the present invention provides antagonist antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol Revs.* 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno* 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of hepsin, MSP and/or hepsin:MSP complex as described herein. Other such antibodies may combine a binding site on these entities with a binding site for another polypeptide. Alternatively, an antibody arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the hepsin and/or MSP-expressing and/or binding cell. Bispecific antibodies may also be used to localize cytotoxic agents to cells which express and/or bind hepsin, MSP and/or hepsin:MSP complex. These antibodies possess a polypeptide binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

9. Immunoconjugates

The invention also pertains to immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):

1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothecene, and CC1065, and the derivatives of these toxins that have toxin activity, are also contemplated herein.

Maytansine and Maytansinoids

In one embodiment, an antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-Maytansinoid Conjugates (Immunoconjugates)

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{113}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tC^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tC^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208, 020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

$$Ab\text{-}(L\text{-}D)_p \qquad \qquad I$$

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, *Bioconjugate Techniques*). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362, 852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

B. Binding Oligopeptides

Binding oligopeptides of the invention are oligopeptides that bind, preferably specifically, to hepsin, MSP and/or hepsin:MSP complex as described herein. Binding oligopeptides may be chemically synthesized using known oligopeptide synthesis methodology or may be prepared and purified using recombinant technology. Binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a target of interest. Binding oligopeptides may be identified without undue experimentation using well known techniques. In this regard, it is noted that techniques for screening oligopeptide libraries for oligopeptides that are capable of specifically binding to a target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

In this regard, bacteriophage (phage) display is one well known technique which allows one to screen large oligopeptide libraries to identify member(s) of those libraries which are capable of specifically binding to a target. Phage display is a technique by which variant polypeptides are displayed as fusion proteins to the coat protein on the surface of bacteriophage particles (Scott, J. K. and Smith, G. P. (1990) *Science*, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA*, 87:6378) or protein (Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene*, 215: 439 (1998); Zhu et al., *Cancer Research*, 58(15): 3209-3214 (1998); Jiang et al., *Infection & Immunity*, 65(11): 4770-4777 (1997); Ren et al., Gene, 195(2):303-311 (1997); Ren, *Protein Sci.*, 5: 1833 (1996); Efimov et al., *Virus Genes*, 10: 173 (1995)) and T7 phage display systems (Smith and Scott, *Methods in Enzymology*, 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. Binding Small Molecules

Binding small molecules are preferably organic molecules other than oligopeptides or antibodies as defined herein that bind, preferably specifically, to hepsin, MSP and/or hepsin: MSP complex as described herein. Binding organic small molecules may be identified and chemically synthesized using known methodology (see, e.g., PCT Publication Nos. WO00/00823 and WO00/39585). Binding organic small molecules are usually less than about 2000 daltons in size, alternatively less than about 1500, 750, 500, 250 or 200 daltons in size, wherein such organic small molecules that are capable of binding, preferably specifically, to a target as described herein may be identified without undue experimentation using well known techniques. In this regard, it is noted that techniques for screening organic small molecule libraries for molecules that are capable of binding to a target are well known in the art (see, e.g., PCT Publication Nos. WO00/00823 and WO00/39585). Binding organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

D. Screening for Antibodies, Binding Oligopeptides and Binding Small Molecules with the Desired Properties Techniques for generating antibodies, oligopeptides and small molecules of the invention have been described above. One may further select antibodies, oligopeptides or other small molecules with certain biological characteristics, as desired.

The inhibitory effects of an antibody, oligopeptide or other small molecule of the invention may be assessed by methods known in the art, e.g., using cells which express hepsin and/or pro-MSP either endogenously or following transfection with the respective gene(s). For example, appropriate tumor cell lines, and hepsin and/or pro-MSP polypeptide-transfected cells may be treated with a monoclonal antibody, oligopeptide or other small molecule of the invention at various concentrations for a few days (e.g., 2-7) days and analyzed for biological activity(ies) known to be associated with MSP activation, including the biological activities assessed according to the Examples below. The antibody, binding oligopeptide or binding organic small molecule will inhibit activity of a hepsin and/or MSP-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Activity inhibition can be measured at an antibody concentration of about 0.5 to 30 µg/ml or about 0.5 nM to 200 nM in cell culture or other suitable experimental system, where the activity inhibition is determined 1-10 days after exposure of the tumor cells to the antibody. The antibody is inhibitory in vivo if administration of the antibody at about 1 µg/kg to about 100 mg/kg body weight results in reduction in tumor size, reduction of tumor cell invasiveness, etc., within about 5 days to 3 months from the first administration of the antibody, preferably within about 5 to 30 days.

To screen for antibodies, oligopeptides or other organic small molecules which bind to an epitope on a target of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody, oligopeptide or other organic small molecule binds the same site or epitope as a known antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a polypeptide can be used in competition assays with the test antibodies or with a test antibody and an antibody with a characterized or known epitope.

E. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 (1984).

F. Antibody Variants

In addition to the antibodies described herein, it is contemplated that antibody variants can be prepared. Antibody variants can be prepared by introducing appropriate nucleotide changes into the encoding DNA, and/or by synthesis of the desired antibody. Those skilled in the art will appreciate that amino acid changes may alter post-translational processes of the antibody, such as changing the number or position of glycosylation sites or altering the membrane anchoring characteristics.

Variations in the antibodies described herein can be made, for example, using any of the techniques and guidelines for conservative and non-conservative mutations set forth, for instance, in U.S. Pat. No. 5,364,934. Variations may be a substitution, deletion or insertion of one or more codons encoding the antibody that results in a change in the amino acid sequence as compared with the native sequence antibody or polypeptide. Optionally the variation is by substitution of at least one amino acid with any other amino acid in one or more of the domains of the antibody. Guidance in determining which amino acid residue may be inserted, substituted or deleted without adversely affecting the desired activity may be found by comparing the sequence of the antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the parent sequence.

Antibody and polypeptide fragments are provided herein. Such fragments may be truncated at the N-terminus or C-terminus, or may lack internal residues, for example, when compared with a full length native antibody or protein. Certain fragments lack amino acid residues that are not essential for a desired biological activity of the antibody or polypeptide.

Antibody and polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR).

Oligonucleotides that define the desired termini of the DNA fragment are employed at the 5' and 3' primers in the PCR. Preferably, antibody and polypeptide fragments share at least one biological and/or immunological activity with the native antibody or polypeptide disclosed herein.

In particular embodiments, conservative substitutions of interest are shown in the table below under the heading of preferred substitutions. If such substitutions result in a change in biological activity, then more substantial changes, denominated exemplary substitutions in this table, or as further described below in reference to amino acid classes, are introduced and the products screened.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the antibody or polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the antibody or polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244:1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

Any cysteine residue not involved in maintaining the proper conformation of the antibody or polypeptide also may be substituted, generally with serine, to improve the oxidative stability of the molecule and prevent aberrant crosslinking. Conversely, cysteine bond(s) may be added to the antibody or polypeptide to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

G. Modifications of Antibodies and Polypeptides

Covalent modifications of antibodies and polypeptides are included within the scope of this invention. One type of covalent modification includes reacting targeted amino acid residues of an antibody or polypeptide with an organic derivatizing agent that is capable of reacting with selected side chains or the N- or C-terminal residues of the antibody or polypeptide. Derivatization with bifunctional agents is useful, for instance, for crosslinking antibody or polypeptide to a water-insoluble support matrix or surface for use in the method for purifying antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the antibody or polypeptide included within the scope of this invention comprises altering the native glycosylation pattern of the antibody or polypeptide. "Altering the native glycosylation pattern" is intended for purposes herein to mean deleting one or more carbohydrate moieties found in native sequence antibody or polypeptide (either by removing the underlying glycosylation site or by deleting the glycosylation by chemical and/or enzymatic means), and/or adding one or more glycosylation sites that are not present in the native sequence antibody or polypeptide. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody or polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody or polypeptide (for O-linked glycosylation sites). The antibody or polypeptide amino acid sequence may optionally be altered through changes at the DNA level, particularly by mutating the DNA encoding the antibody or polypeptide at preselected bases such that codons are generated that will translate into the desired amino acids.

Another means of increasing the number of carbohydrate moieties on the antibody or polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the antibody or polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of antibody or polypeptide comprises linking the antibody or polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

The antibody or polypeptide of the present invention may also be modified in a way to form chimeric molecules comprising an antibody or polypeptide fused to another, heterologous polypeptide or amino acid sequence.

In one embodiment, such a chimeric molecule comprises a fusion of the antibody or polypeptide with a tag polypeptide which provides an epitope to which an anti-tag antibody can selectively bind. The epitope tag is generally placed at the amino- or carboxyl-terminus of the antibody or polypeptide. The presence of such epitope-tagged forms of the antibody or polypeptide can be detected using an antibody against the tag polypeptide. Also, provision of the epitope tag enables the antibody or polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the antibody or polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an antibody or polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule. For the production of immunoglobulin fusions see also U.S. Pat. No. 5,428, 130 issued Jun. 27, 1995.

H. Preparation of Antibodies and Polypeptides

The description below relates primarily to production of antibodies and polypeptides by culturing cells transformed or transfected with a vector containing antibody- and polypeptide-encoding nucleic acid. It is, of course, contemplated that alternative methods, which are well known in the art, may be employed to prepare antibodies and polypeptides. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the antibody or polypeptide may be chemically synthesized separately and combined using chemical or enzymatic methods to produce the desired antibody or polypeptide.

1. Isolation of DNA Encoding Antibody or Polypeptide

DNA encoding antibody or polypeptide may be obtained from a cDNA library prepared from tissue believed to possess the antibody or polypeptide mRNA and to express it at a detectable level. Accordingly, human antibody or polypeptide DNA can be conveniently obtained from a cDNA library prepared from human tissue. The antibody- or polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding antibody or polypeptide is to use PCR methodology [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for antibody or polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full-length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g, in CHO cells.

In addition to prokaryotes, eukaryotic microbes such as filamentous fungi or yeast are suitable cloning or expression hosts for antibody- or polypeptide-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81:1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated antibody or polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR(CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody or polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding antibody or polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the antibody- or polypeptide-encoding DNA that is inserted into the vector. The signal sequence may be a prokaryotic signal sequence selected, for example, from the group of the alkaline phosphatase, penicillinase, 1 pp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the antibody- or polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the antibody- or polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (tip) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding antibody or polypeptide.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Antibody or polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the antibody or polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antibody or polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody or polypeptide.

Still other methods, vectors, and host cells suitable for adaptation to the synthesis of antibody or polypeptide in recombinant vertebrate cell culture are described in Gething et al., *Nature*, 293:620-625 (1981); Mantei et al., *Nature*, 281:40-46 (1979); EP 117,060; and EP 117,058.

4. Culturing the Host Cells

The host cells used to produce the antibody or polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCINT™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence polypeptide or against a synthetic peptide based on the DNA sequence provided herein or against exogenous sequence fused to polypeptide DNA and encoding a specific antibody epitope.

6. Purification of Antibody and Polypeptide

Forms of antibody and polypeptide may be recovered from culture medium or from host cell lysates. If membrane-bound, it can be released from the membrane using a suitable detergent solution (e.g. Triton-X 100) or by enzymatic cleavage. Cells employed in expression of antibody and polypeptide can be disrupted by various physical or chemical means, such as freeze-thaw cycling, sonication, mechanical disruption, or cell lysing agents.

It may be desired to purify antibody and polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the antibody and polypeptide. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular antibody or polypeptide produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

I. Pharmaceutical Formulations

Therapeutic formulations of the antibodies, binding oligopeptides, binding organic or inorganic small molecules and/or polypeptides used in accordance with the present invention are prepared for storage by mixing the antibody, polypeptide, oligopeptide or organic/inorganic small molecule having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The formulation may comprise the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to an antibody, binding oligopeptide, or binding organic or inorganic small molecule, it may be desirable to include in the one formulation, an additional antibody, e.g., a second antibody which binds a different epitope on the same polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*, 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

J. Treatment with Antibodies, Binding Oligopeptides and Binding Organic/Inorganic Small Molecules To determine polypeptide (hepsin and/or MSP) expression in the cancer, various detection assays are available. In one embodiment, polypeptide overexpression may be analyzed by immunohistochemistry (IHC). Parrafin embedded tissue sections from a tumor biopsy may be subjected to the IHC assay and accorded a polypeptide staining intensity criteria as follows:

Score 0—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for polypeptide expression may be characterized as not overexpressing the polypeptide, whereas those tumors with 2+ or 3+ scores may be characterized as overexpressing the polypeptide.

Alternatively, or additionally, FISH assays such as the INFORM® (sold by Ventana, Arizona) or PATHVISION® (Vysis, Ill.) may be carried out on formalin-fixed, paraffin-embedded tumor tissue to determine the extent (if any) of polypeptide overexpression in the tumor.

Polypeptide overexpression or amplification may be evaluated using an in vivo detection assay, e.g., by administering a molecule (such as an antibody, oligopeptide or organic small molecule) which binds the molecule to be detected and is tagged with a detectable label (e.g., a radioactive isotope or a fluorescent label) and externally scanning the patient for localization of the label.

As described above, the antibodies, oligopeptides and organic/inorganic small molecules of the invention have various non-therapeutic applications. The antibodies, oligopeptides and organic/inorganic small molecules of the present invention can be useful for staging of polypeptide-expressing cancers (e.g., in radioimaging). The antibodies, oligopeptides and organic/inorganic small molecules are also useful for purification or immunoprecipitation of polypeptide from cells, for detection and quantitation of polypeptide in vitro, e.g., in an ELISA or a Western blot, to kill and eliminate polypeptide-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Antibody, oligopeptide or organic/inorganic small molecule therapy may be especially desirable in elderly patients who do not tolerate the toxicity and side effects of chemotherapy well and in metastatic disease where radiation therapy has limited usefulness. The tumor targeting antibodies, oligopeptides and organic/inorganic small molecules of the invention are useful to alleviate polypeptide-expressing cancers upon initial diagnosis of the disease or during relapse. For therapeutic applications, the antibody, oligopeptide or organic/inorganic small molecule can be used alone, or in combination therapy with, e.g., hormones, antiangiogenics, or radiolabelled compounds, or with surgery, cryotherapy, and/or radiotherapy. Antibody, oligopeptide or organic/inorganic small molecule treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered antibody, oligopeptide or organic/inorganic small molecule in conjunction with treatment with the one or more of the preceding chemotherapeutic agents. In particular, combination therapy with palictaxel and modified derivatives (see, e.g., EP0600517) is contemplated. The antibody, oligopeptide or organic/inorganic small molecule will be administered with a therapeutically effective dose of the chemotherapeutic agent. In another embodiment, the antibody, oligopeptide or organic/inorganic small molecule is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an antibody, oligopeptide or organic/inorganic small molecule conjugated with a cytotoxic agent is administered to the patient. Preferably, the immunoconjugate bound to the protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The antibodies, oligopeptides, organic/inorganic small molecules or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, oligopeptide or organic/inorganic small molecule is preferred.

Other therapeutic regimens may be combined with the administration of the antibody, oligopeptide or organic/inorganic small molecule. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the antibody or antibodies, oligopeptides or organic/inorganic small molecules, with administration of an antibody directed against another tumor antigen associated with the particular cancer.

In another embodiment, the therapeutic treatment methods of the present invention involves the combined administration of an antibody (or antibodies), oligopeptides or organic/inorganic small molecules and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody, oligopeptide or organic/inorganic small molecule may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the antibody, oligopeptide or organic/inorganic small molecule (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody, oligopeptide or organic/inorganic small molecule therapy. Suitable dosages for any of the above co-administered agents are those presently used and may be lowered due to the combined action (synergy) of the agent and antibody, oligopeptide or organic/inorganic small molecule.

For the prevention or treatment of disease, the dosage and mode of administration will be chosen by the physician according to known criteria. The appropriate dosage of antibody, oligopeptide or organic/inorganic small molecule will depend on the type of disease to be treated, as defined above, the severity and course of the disease, whether the antibody, oligopeptide or organic/inorganic small molecule is administered for preventive or therapeutic purposes, previous therapy, the patient's clinical history and response to the antibody, oligopeptide or organic/inorganic small molecule, and the discretion of the attending physician. The antibody, oligopeptide or organic/inorganic small molecule is suitably administered to the patient at one time or over a series of treatments. Preferably, the antibody, oligopeptide or organic/inorganic small molecule is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., *Science* 256:808-813 (1992). See also WO 93/25673 and the references cited therein.

The antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present antibodies of the invention are also contemplated, specifically including the in vivo tumor targeting and any cell proliferation inhibition or cytotoxic characteristics.

Methods of producing the above antibodies are described in detail herein.

The present antibodies, oligopeptides and organic/inorganic small molecules are useful for treating a hepsin and/or MSP-expressing cancer, or alleviating one or more symptoms of the cancer in a mammal. Methods of the invention encompass usage of antagonists in the treatment and/or alleviation of symptoms of metastatic tumors associated with these cancers. The antibody, oligopeptide or organic/inorganic small molecule antagonist is able to bind to at least a portion of the cancer cells that express the polypeptide(s) (hepsin and/or MSP) in the mammal. In one embodiment, the antibody, oligopeptide or organic/inorganic small molecule is effective to cause destruction or killing of polypeptide-expressing and/or -responsive tumor cells, or inhibit the growth and/or invasiveness of such tumor cells, in vitro or in vivo, upon binding to the polypeptide. Such an antibody includes a naked antibody (not conjugated to any agent). Naked antibodies that have cytotoxic or other inhibition properties can be further harnessed with a cytotoxic agent to render them even more potent in tumor cell destruction. Cytotoxic properties can be conferred to an antibody by, e.g., conjugating the antibody with a cytotoxic agent, to form an immunoconjugate as described herein. In some embodiments, the cytotoxic agent or a growth inhibitory agent is a small molecule. In some embodiments, toxins such as calicheamicin or a maytansinoid and analogs or derivatives thereof, are used.

The invention provides a composition comprising an antibody, oligopeptide or organic/inorganic small molecule of the invention, and a carrier. For the purposes of treating cancer, compositions can be administered to the patient in need of such treatment, wherein the composition can comprise one or more antibodies present as an immunoconjugate or as the naked antibody. In a further embodiment, the compositions can comprise these antibodies, oligopeptides or organic/inorganic small molecules in combination with other therapeutic agents such as cytotoxic or growth inhibitory agents, including chemotherapeutic agents. The invention also provides formulations comprising an antibody, oligopeptide or organic/inorganic small molecule of the invention, and a carrier. In one embodiment, the formulation is a therapeutic formulation comprising a pharmaceutically acceptable carrier.

Another aspect of the invention is isolated nucleic acids encoding the antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a cancer or alleviating one or more symptoms of the cancer in a mammal, comprising administering a therapeutically effective amount of an antibody, oligopeptide or organic/inorganic small molecule to the mammal. The antibody, oligopeptide or organic/inorganic small molecule therapeutic compositions can be administered short term (acute) or chronic, or intermittent as directed by physician. Also provided are methods of inhibiting the growth of, and killing a polypeptide (hepsin and/or MSP)-expressing and/or -responsive cell.

The invention also provides kits and articles of manufacture comprising at least one antibody, oligopeptide or organic/inorganic small molecule. Kits containing antibodies, oligopeptides or organic/inorganic small molecules find use, e.g., for cell killing assays, for inhibiting tumor cell invasion, and for purification or immunoprecipitation of polypeptide from cells. For example, for isolation and purification of a polypeptide, the kit can contain an antibody, oligopeptide or organic/inorganic small molecule coupled to beads (e.g., sepharose beads). Kits can be provided which contain the antibodies, oligopeptides or organic/inorganic small molecules for detection and quantitation of a polypeptide in vitro, e.g., in an ELISA or a Western blot. Such antibody, oligopeptide or organic/inorganic small molecule useful for detection may be provided with a label such as a fluorescent or radiolabel.

K. Articles of Manufacture and Kits

Another embodiment of the invention is an article of manufacture containing materials useful for the treatment of a polypeptide (hepsin and/or MSP) expressing cancer, such as prostate and ovarian cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an antibody, oligopeptide or organic/inorganic small molecule of the invention. The label or package insert indicates that the composition is used for treating cancer. The label or package insert will further comprise instructions for administering the antibody, oligopeptide or organic/inorganic small molecule composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for polypeptide-expressing or cell killing assays, for purification or immunoprecipitation of a polypeptide from cells. For isolation and purification of a polypeptide, the kit can contain an antibody, oligopeptide or organic/inorganic small molecule coupled to beads (e.g., sepharose beads). Kits can be provided which contain the antibodies, oligopeptides or organic/inorganic small molecules for detection and quantitation of a polypeptide in vitro, e.g., in an ELISA or a Western blot. As with the article of manufacture, the kit comprises a container and a label or package insert on or associated with the container. The container holds a composition comprising at least one antibody, oligopeptide or organic/inorganic small molecule of the invention. Additional containers may be included that contain, e.g., diluents and buffers, control antibodies. The label or package insert may provide a description of the composition as well as instructions for the intended in vitro or detection use.

L. Polypeptides and Polypeptide-Encoding Nucleic Acids—Specific Forms and Applications Nucleotide sequences (or their complement) encoding polypeptides of the invention have various applications in the art of molecular biology, as well as uses for therapy, etc. Polypeptide-encoding nucleic acid will also be useful for the preparation of polypeptides by the recombinant techniques described herein, wherein those polypeptides may find use, for example, in the preparation of antibodies as described herein.

A full-length native sequence polypeptide gene, or portions thereof, may be used as hybridization probes for a cDNA library to isolate other cDNAs (for instance, those encoding naturally-occurring variants of a polypeptide or a polypeptide from other species) which have a desired sequence identity to a native polypeptide sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence polypeptide. By way of example, a screening method will comprise isolating the coding region of the polypeptide gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the polypeptide gene of the present invention can be used to screen libraries of human cDNA, genomic DNA or mRNA to determine which members of such libraries the probe hybridizes to. Hybridization techniques are described in further detail in the Examples below. Any EST sequences disclosed in the present application may similarly be employed as probes, using the methods disclosed herein.

Other useful fragments of the polypeptide-encoding nucleic acids include antisense or sense oligonucleotides comprising a singe-stranded nucleic acid sequence (either RNA or DNA) capable of binding to target a polypeptide mRNA (sense) or a polypeptide DNA (antisense) sequence. Antisense or sense oligonucleotides, according to the present invention, comprise a fragment of the coding region of a DNA encoding hepsin, pro-MSP or binding fragments as described herein. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of a protein, wherein the protein may play a role in the induction of cancer in mammals. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of preferred antisense compounds useful for inhibiting expression of a polypeptide include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3',5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Representative United States patents that teach the preparation of such oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred antisense oligonucleotides incorporate phosphorothioate backbones and/or heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[$(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred antisense oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim Acta, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$).

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873;

5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$ or —CH$_2$—C≡CH) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido [5,4-b][1,4]benzoxazin-2(3H)-one), phenothiazine cytidine (1H-pyrimido[5,4-b][1,4]benzothiazin-2(3H)-one),
G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',':4,5]pyrrolo[2,3-d] pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613. Certain of these nucleobases are particularly useful for increasing the binding affinity of the oligomeric compounds of the invention. These include 5-substituted pyrimidines, 6-azapyrimidines and N2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi et al, Antisense Research and Applications, CRC Press, Boca Raton, 1993, pp. 276-278) and are preferred base substitutions, even more particularly when combined with 2'-O-methoxyethyl sugar modifications. Representative United States patents that teach the preparation of modified nucleobases include, but are not limited to: U.S. Pat. No. 3,687,808, as well as U.S. Pat. Nos. 4,845,205; 5,130, 302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim Biophys. Acta, 1995, 1264, 229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) and U.S. Pat. Nos. 4,828, 979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Preferred chimeric antisense oligonucleotides incorporate at least one 2' modified sugar (preferably 2'-O—$(CH_2)_2$—O—$CH_3$) at the 3' terminal to confer nuclease resistance and a region with at least 4 contiguous 2'-H sugars to confer RNase H activity. Such compounds have also been referred to in the art as hybrids or gapmers. Preferred gapmers have a region of 2' modified sugars (preferably 2'-O—$(CH_2)_2$—O—$CH_3$) at the 3'-terminal and at the 5' terminal separated by at least one region having at least 4 contiguous 2'-H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

The probes may also be employed in PCR techniques to generate a pool of sequences for identification of closely related polypeptide coding sequences.

Nucleotide sequences encoding a polypeptide can also be used to construct hybridization probes for mapping the gene which encodes that polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

The polypeptide can be used in assays to identify other proteins or molecules involved in a binding interaction with the polypeptide. By such methods, inhibitors of the receptor/ligand binding interaction can be identified. Proteins involved in such binding interactions can also be used to screen for peptide or small molecule inhibitors of the binding interaction. Screening assays can be designed to find lead compounds that mimic the biological activity of a native polypeptide or a receptor for the polypeptide. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode a polypeptide or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a polypeptide can be used to clone genomic DNA encoding the polypeptide in accordance with established techniques and the genomic sequences used to generate transgenic animals that contain cells which express DNA encoding the polypeptide. Methods for generating transgenic animals, particularly animals such as mice or rats, have become conventional in the art and are described, for example, in U.S. Pat. Nos. 4,736,866 and 4,870,009. Typically, particular cells would be targeted for polypeptide transgene incorporation with tissue-specific enhancers. Transgenic animals that include a copy of a transgene encoding a polypeptide introduced into the germ line of the animal at an embryonic stage can be used to examine the effect of increased expression of DNA encoding a polypeptide. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of a polypeptide can be used to construct a a gene "knock out" animal which has a defective or altered gene encoding the polypeptide as a result of homologous recombination between the endogenous gene encoding the polypeptide and altered genomic DNA encoding the polypeptide introduced into an embryonic stem cell of the animal. For example, cDNA encoding the polypeptide can be used to clone genomic DNA encoding the polypeptide in accordance with established techniques. A portion of the genomic DNA encoding the polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

Nucleic acid encoding the polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The nucleic acid molecules encoding the polypeptides or fragments thereof described herein are useful for chromosome identification. In this regard, there exists an ongoing need to identify new chromosome markers, since relatively few chromosome marking reagents, based upon actual sequence data are presently available. Each nucleic acid molecule of the present invention can be used as a chromosome marker.

Polypeptides and nucleic acid molecules of the invention may be used diagnostically for tissue typing, wherein the polypeptides may be differentially expressed in one tissue as compared to another, preferably in a diseased tissue as compared to a normal tissue of the same tissue type. Nucleic acid molecules will find use for generating probes for PCR, Northern analysis, Southern analysis and Western analysis.

This invention encompasses methods of screening compounds to identify those that prevent the effect of the polypeptide (antagonists). Screening assays for antagonist drug candidates are designed to identify compounds that bind or complex with the polypeptides encoded by the genes identified herein, or otherwise interfere with the interaction of the encoded polypeptides with other cellular proteins, including e.g., inhibiting the expression of the polypeptide from cells. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a polypeptide or polypeptide complex under conditions and for a time sufficient to allow these components to interact.

In binding assays, the interaction is binding and the complex formed can be isolated or detected in the reaction mixture. In a particular embodiment, the polypeptide or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a polypeptide, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the polypeptide may be added to a cell along with the compound to be screened for a particular activity and the ability of the compound to inhibit the activity of interest in the presence of the polypeptide indicates that the compound is an antagonist to the polypeptide. Alternatively, antagonists may be detected by combining the polypeptide and a potential antagonist with membrane-bound polypeptide receptors or encoded receptors under appropriate conditions for a competitive inhibition assay. The polypeptide can be labeled, such as by radioactivity, such that the number of polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the polypeptide and a cDNA library created from this RNA is divided into pools and used to transfect COS cells or other cells that are not responsive to the polypeptide. Transfected cells that are grown on glass slides are exposed to labeled polypeptide. The polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

More specific examples of potential antagonists include antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the polypeptide that recognizes the receptor but imparts no effect, thereby competitively inhibiting the action of the polypeptide.

Another potential antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides herein, can be used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the polypeptide. The antisense RNA oligonucleotide hybridizes to the mRNA in vivo and blocks translation of the mRNA molecule into the polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the polypeptide, thereby blocking the normal biological activity of the polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Isolated polypeptide-encoding nucleic acid can be used for recombinantly producing polypeptide using techniques well known in the art and as described herein. In turn, the produced polypeptides can be employed for generating antibodies using techniques well known in the art and as described herein.

Antibodies specifically binding a polypeptide identified herein, as well as other molecules identified by the screening assays disclosed hereinbefore, can be administered for the treatment of various disorders, including cancer, in the form of pharmaceutical compositions.

If the polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

EXAMPLES

Materials and Methods

Cloning, expression and purification of recombinant proteins: The extracellular domain of the human recombinant hepsin was expressed and purified as described (Moran et al., 2006). Anti-hepsin antibody Fab25 was expressed and purified as described in co-pending, co-owned U.S. provisional patent application No. 61/253,953, filed Oct. 22, 2009. Recombinant human MSP that comprised a C672A mutation to improve expression and yield was expressed in Chinese Hamster Ovary cells as described (Wahl et al., 1997). KD1 was expressed and purified as described (Shia et al., 2005).

Analysis of in vitro activation of pro-msp by hepsin using sds-page: Pro-MSP (25 μg/ml) was incubated with different concentrations of hepsin (1.25 nM, 2.5 nM, 5 nM and 10 nM) in a buffer containing 50 mM Tris-HCl pH 8.0, 150 mM NaCl, 0.05% Triton-X100 and 2 mM $CaCl_2$ at 37° C. Aliquots of the reaction mixture at different time points were mixed 6×-SDS sample buffer and the samples were boiled for 5 minutes at 95° C. and separated by SDS-PAGE using a 4-20% gradient gel. Protein was visualized after staining with SimplyBlue Safe Stain (Invitrogen, Carlsbad, Calif.). Similar experiments were performed with the pro-MSP that was mutated to render it uncleavable at $Arg_{483}$-$Val_{484}$(pro-MSP-R483E) to assess if proteolytic cleavage site occurs at a different site apart from the expected $Arg_{483}$-$Val_{484}$ bond in pro-MSP.

Pro-MSP activation by cell surface expressed hepsin in LnCap cells: The LnCaP-34 cells were generated as described (Moran et al., 2006), to stably overexpress hepsin resulting in 5-fold increased hepsin cell surface expression and 3-fold increased hepsin enzymatic activity compared to the LnCaP-17 cells, which only express endogenous hepsin at relatively low levels, comparable to the parental LnCaP cells. Confluent LnCap-34 cells cultured in 24-well plates were washed with serum-free RPMI-1640 medium and were incubated either alone or with different anti-hepsin inhibitors (1 µM of anti-hepsin antibody Fab25/1 µM of KD1/1 µM of Ac-KQLR-cmk ('KLQR" disclosed as SEQ ID NO:10)) in serum-free RPMI-1640 medium for 15 minutes at 37° C. prior to addition of 125I-labeled pro-MSP (25 µg/ml). After incubation for 3 hours at 37° C., aliquots were removed and analyzed by SDS-PAGE (4-20% gradient gel) (Invitrogen, Carlsbad, Calif.) followed by exposure to X-ray films.

Binding of hepsin-activated pro-MSP to Ron by surface plasmon resonance and ELISA: To determine binding affinity of hepsin-activated MSP to human Ron, surface plasmon resonance measurements on a BIAcore™-3000 instrument (GE Health Care, NJ) were performed. Rabbit anti-human IgG were chemically immobilized (amine coupling) on CM5 biosensor chips and the Ron (Sema IPT1)-IgG fusion protein was captured to give approximately 250 response units (RU). For kinetics measurements, different concentration of either hepsin-activated MSP or a commercially available MSP (R&D systems) were injected in HBS-P buffer at 25° C. with a flow rate of 30 µl/min. Association rates ($k_{on}$) and dissociation rates ($k_{off}$) were obtained by using a simple one-to-one Langmuir binding model (BIA-Evaluation) and the equilibrium dissociation constants ($K_D$) were calculated ($k_{off}/k_{on}$). For ELISA experiments, maxiSorp microtiter plates (Nunc, Roskilde, Denmark) were coated overnight at 4° C. with 2 µg/ml of rabbit anti-human IgG Fc specific antibody (Jackson ImmunoResearch Laboratory, West Grove, Pa.) in 50 mM sodium carbonate buffer, pH 9.6. After blocking with assay buffer (PBS pH 7.4, 0.5% BSA and 0.05% Tween-20, 15 PPM Proclin), 1 µg/ml Ron (Sema IPT1)-IgG fusion protein was added and plates were incubated for 1 hour with gentle shaking at room temperature. After washing with wash buffer (PBS, 0.05% polysorbate 20), His tagged MSP proteins were added for 1 hour. Bound MSP was detected using anti-His-HRP (Qiagen, Valencia, Calif.) followed by addition of TMB/ $H_2O_2$ substrate (KPL, Gaithersburg, Md.). The reaction was stopped with 1M $H_3PO_4$ and the $A_{450}$ was measured on a Molecular Devices (Sunnyvale, Calif.) SpectraMax Plus$^{384}$ microplate reader. The effective concentration to give half-maximal binding ($EC_{50}$) was determined by a four parameter fit using Kaleidagraph (Synergy Software, Reading, Pa.).

Peritoneal macrophage chemotaxis and morphology change assay: Murine peritoneal resident macrophages were obtained from C57BL/6 mice by washing the peritoneal cavity with 15 ml per mouse of serum-free RPMI-1640 medium. Cells were washed and resuspended in RPMI-1640 medium containing 25 mM Hepes at a concentration of $1 \times 10^6$ cells·mL$^{-1}$. The macrophage chemotaxis assay was performed using a QCM chemotaxis assay kit with a pore size of 5 µm (Millipore). One hundred microliters of the peritoneal macrophage suspension (i.e. $10^5$ cells) were added to the upper wells of the Chemotaxis cells. The bottom wells were filled with RPMI-1640 medium containing purified pro-MSP either alone or hepsin-treated at 37 C for 2 hours. The recombinant active form of human MSP (R&D Systems) was used as a positive control. After incubation at 37 C for 4 hours, the cells on the upper surface of the membrane were wiped off with a cotton swab and the migrated cells were detached using detachment buffer as per manufacturer's recommendations. Aliquots from different wells were incubated with a mixture of lysis buffer and CYPRO dye for 15 minutes. Migration was quantified by measuring the fluorescence using a microplate reader (Spectramax-M5, Molecular devices, Sunnyvale, Calif.) at an excitation wavelength of 480 nm and emission wavelength of 520 nm.

To assess the effect of MSP on the morphology, peritoneal macrophages ($1 \times 10^6$ cells·mL$^{-1}$) were cultured in serum-free RPMI-1640 medium overnight. After incubation, non-adherent cells were removed and pro-MSP (1.0 nM), either alone or pretreated with hepsin, was added to the culture medium. After an additional incubation at 37 C for 1 hour, morphological changes of the macrophages were observed by phase-contrast microscopy.

Inhibition of NO synthesis by mature MSP: Bone marrow cells obtained from collected mouse femurs were pipetted to a single-cell suspension and then spun down. Red blood cells were lysed by incubation with erythrocyte lysis buffer for 5 minutes at room temperature. Cells were then suspended in macrophage differentiation medium (DMEM with glutamine containing 10% FBS, Pen/Strep and 50 ng/ml recombinant mCSF-1). Cells were then plated onto sterile 24-well non-tissue culture dishes. Medium was changed the next day and subsequently every 2 days. After 6 days in culture, the macrophages were mature and these mature cells were washed in serum-free DMEM and further incubated for 2 hours. Different reactions (total volume 300 µL) as indicated in the figure consisting of recombinant MSP (10 ng/ml), pro-MSP (10 ng/ml), hepsin (1 nM) and Fab25 (500 nM) were added to the respective wells and cultured for 24 hours at 37° C. in a tissue culture incubator. NO production was quantified using Griess reaction (Molecular Probes) according to manufacturer's recommendation.

Immunoblot for the detection of phosphorylated kinases: A human ovarian carcinoma cell line (A2780) overexpressing human Ron was used to study the phosphorylation of Ron and other downstream kinase. Cells at a density of $2 \times 10^5$ cells/well were cultured in 12-well plate and serum-starved for 24 hours. The cells were then stimulated with either pro-MSP (10 and 50 ng/ml) alone or in presence of 10 nM Hepsin for 1 hour. Mature MSP from a commercial source and hepsin were used as controls. Samples were prepared by washing cells twice with cold PBS followed by addition of 200 ul lysis buffer. Samples were then analyzed by SDS/PAGE on 4-12% Tris-glycine gels (Invitrogen, Carlsbad, Calif.). Proteins were transferred onto nitrocellulose membranes and subsequently treated with anti-Ron antibody or anti-phospho-AKT antibody or anti-phospho-MAPK antibody or anti-phospho-S6 antibody, overnight at 4° C. After washing, membranes were incubated with IRDye800-conjugated goat anti-mouse IgG (Rockland, Gilbertsville, Pa.) and AlexaFluor 680 goat anti-rabbit IgG (Invitrogen) for 1 h. Proteins were detected with the Odyssey Infrared Imaging System (LI-COR Biosciences, Lincoln, Nebr.).

Results

In vitro Activation of pro-MSP by Recombinant Hepsin

A consensus sequence based on the substrate profiling for hepsin by PS-SCL (positional scanning-synthetic combinatorial library) revealed a preference for P4-P1 as (P/K)-(K/Q)-(T/L/N)-R (Herter et al., 2005). It is evident from the list of previously identified hepsin-substrates (Kazama et al., 1995; Kirchhofer et al., 2005; Moran et al., 2006; Tripathi et al., 2008) (Table 1), that the cleavage site sequences are mostly in agreement with the PS-SCL substrate profiling. In particular the substrate recognition sequences for proHGF (KQLR↓V) (SEQ ID NO: 11) and Ln-332 (SQLR↓L) (SEQ ID NO: 12) bear close resemblance with the cleavage sequence of pro-MSP (SKLR↓V) (SEQ ID NO: 1). However, such reasoning fails to explain why another zymogen, pro-tPA, is a poor hepsin substrate, because the recognition sequence is a hybrid of those from pro-HGF and pro-uPA (Table 1).

TABLE 1

| | Recognition sequence | SEQ ID NO: |
|---|---|---|
| Hepsin substrates | | |
| Pro-MSP | SKLR↓V | 1 |
| Pro-HGF | KQLR↓V | 11 |
| Ln-332 | SQLR↓L | 12 |
| Pro-uPA | PRFK↓I | 13 |
| FVII | PQGR↓I | 14 |
| PS-SCL | (P/K)-(K/Q)-(T/L/N)-R | |
| Hepsin resistant substrates | | |
| Pro-tPA | PQFR↓I | 15 |
| Plasminogen | CPGR↓V | 16 |

↓ indicates cleavage site

Hepsin activated pro-MSP in a dose-dependent and time dependent manner upon incubation with different concentrations of hepsin at 37° C. The activation was monitored by gel-mobility shift on 4-20% gradient Tris-glycine SDS-PAGE under reducing condition (FIG. 1). The cleavage products were analyzed by N-terminal sequencing to identify the processing site. Proteolytic cleavage of pro-MSP by hepsin occurred at Arg483-Val484 bond, resulting in the formation of an active MSP (α/β) heterodimeric. A cleavage-site mutant of pro-MSP (pro-MSP-R483E) was expressed and purified and was subjected to proteolytic processing by hepsin. Hepsin did not cleave this mutant pro-MSP despite prolonged incubation (24 hours) reconfirming the specificity of the activation.

Pro-MSP Activation by Cell Surface-expressed Hepsin

Figure 2:
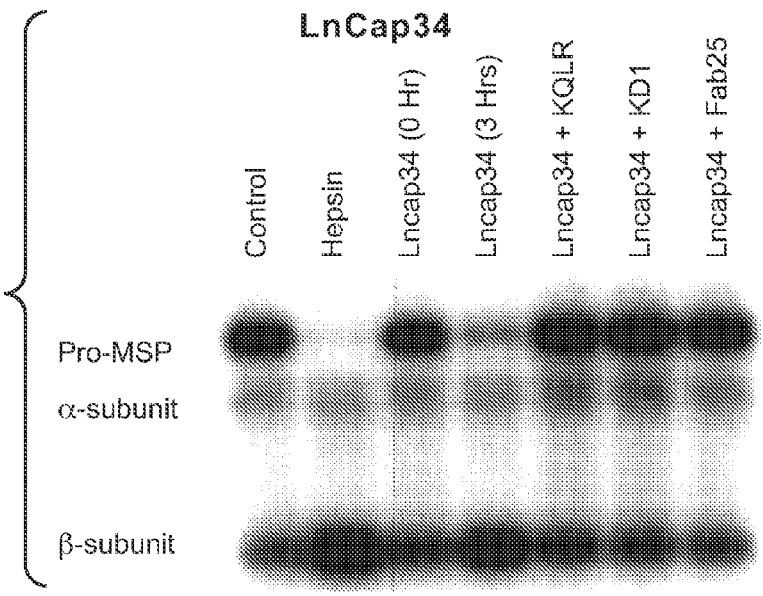
FIG. 2: Activation of pro-MSP by cell surface expressed hepsin in LnCap-34 cells. LnCap-34 cells which stably overexpress hepsin were serum starved and treated with $^{125}$I-pro-MSP alone or in combination with different inhibitors for 3 hours. Recombinant hepsin (10 nM) was used as a positive control. Significant increase in pro-MSP processing was observed after 3 hours compared to the start of the experiment Inhibitors KQLR (SEQ ID NO 10), KD1 and anti-hepsin antibody Fab25 effectively blocked the activation of pro-MSP.

Proteolytic processing of pro-MSP by natively expressed hepsin on the cell surface was monitored on the LnCap-34 cell line (Moran et al., 2006). LnCap-34 cells expressing hepsin was capable of processing the $^{125}$I-pro-MSP (FIG. 2). The proteolytic activity of pro-MSP processing was mainly due to hepsin as all the three hepsin inhibitors (Ac-KQLR-chloromethylketone ('KQLR; disclosed as SEQ ID NO: 10), KD1 and Fab25) effectively blocked the proteolytic cleavage.

Biological Activity of Hepsin-Activated MSP

MSP Binding to Ron

Figure 3A:
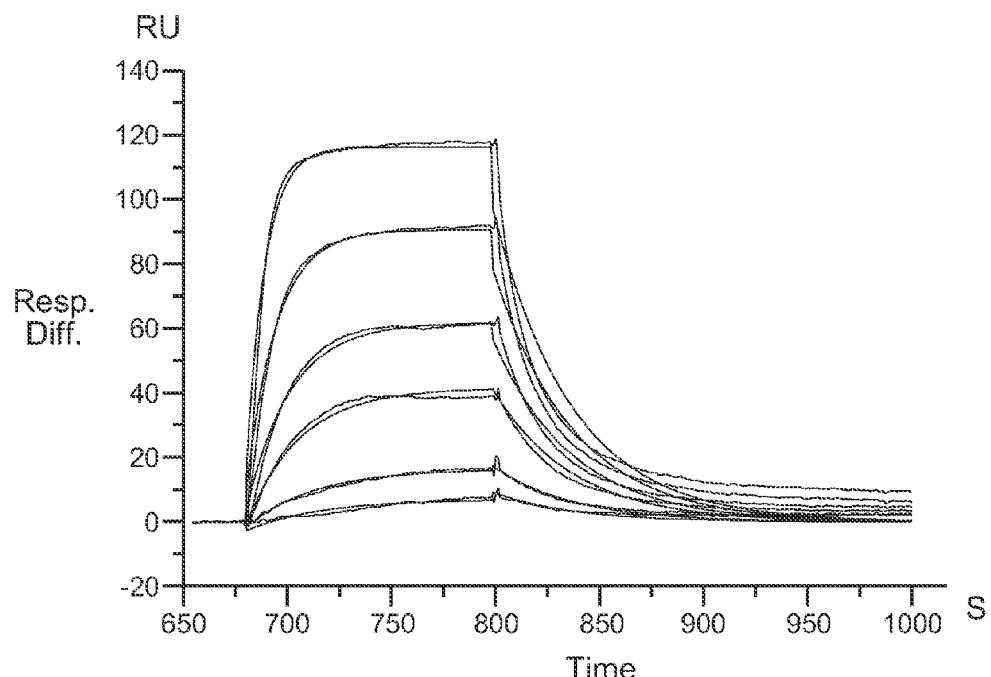
FIG. 3: Binding of hepsin-activated MSP to Ron. (a) For surface plasmon resonance experiment, CM5 chip which was amine coupled with an anti-Fc specific antibody was used to capture Ron-Fc on the biosensor. No detectable binding of pro-MSP (1 µM) to Ron was observed while hepsin-activated MSP showed high affinity binding ($K_D$ 7 nM) to Ron, the data was fitted with a 1:1 binding model. (b) In the ELISA experiment to measure the binding of MSP to Ron, the determined effective concentration to give half-maximal binding ($EC_{50}$) was 0.519 nM.
Figure 3B:
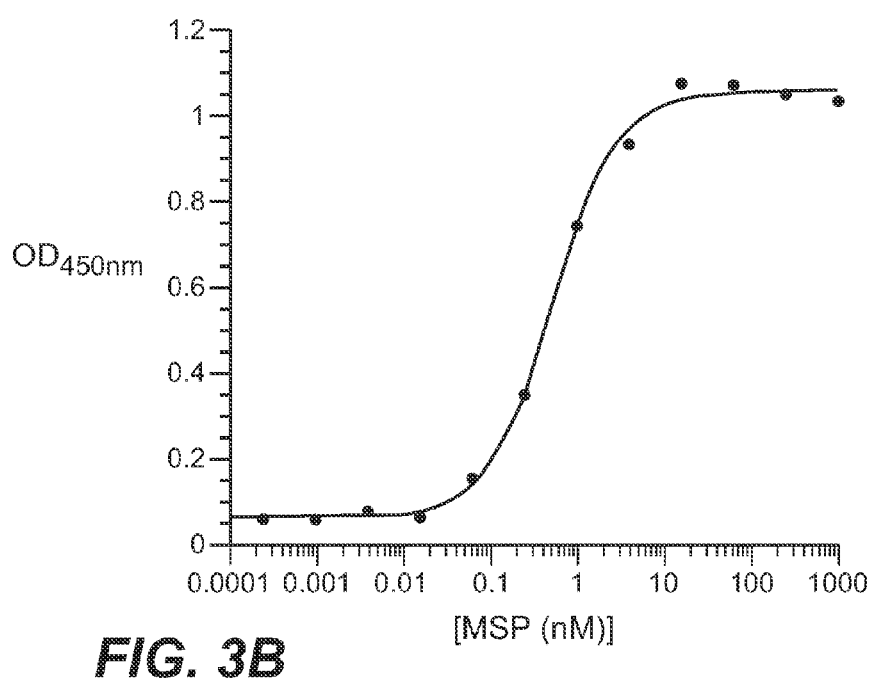
Figure 4:
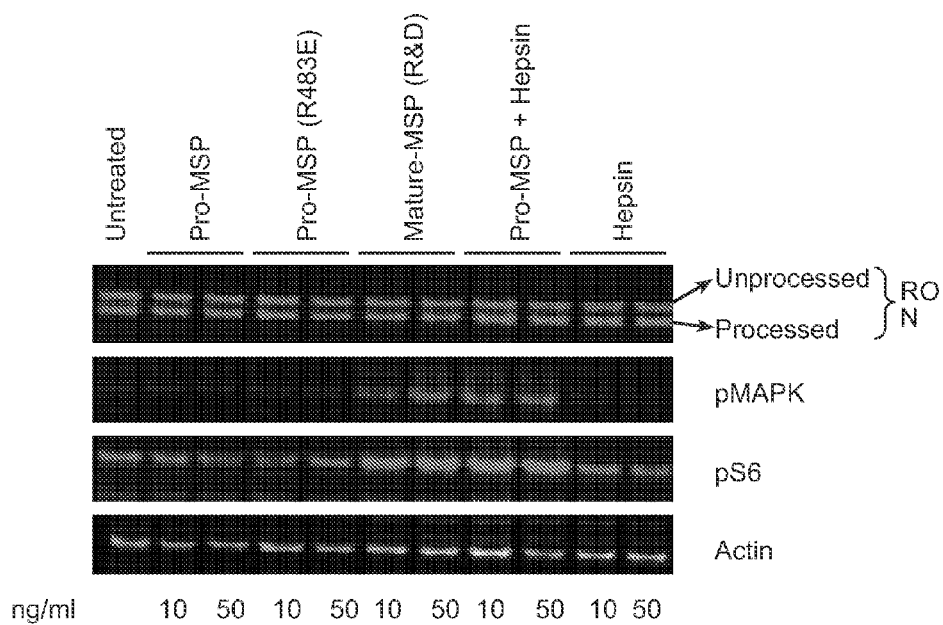
FIG. 4: Phosphorylation of S6 and MAP kinase. Neither hepsin nor pro-MSP alone was effective in activating Ron signaling pathway, while hepsin treatment of pro-MSP showed robust phosphorylation of both MAP kinase and S6 kinase in a dose dependent manner.

We used surface-plasmon resonance (BIAcore) to determine the binding affinity of MSP to human Ron. Proteolytic cleavage of the single-chain pro-MSP is critical for binding to the receptor Ron. Neither pro-MSP nor the cleavage site mutant (pro-MSP-R483E) had any detectable binding to Ron up to a concentration of 1 μM. In contrast, hepsin-activated MSP displayed high affinity binding to Ron ($K_D$=7 nM) (FIG. 3a). The affinity of hepsin-activated MSP was very similar to a commercially available MSP ($K_D$=4.4 nM). Additionally, we measured the binding of MSP to Ron in ELISA experiments. The determined effective concentration to give half-maximal binding ($EC_{50}$) was 0.519 nM (FIG. 3b).

Phosphorylation of Downstream Kinases in MSP/RON Pathway

The biological effects of hepsin-treated pro-MSP on the Ron signaling pathway were monitored by the following the phosphorylation of downstream kinases which include the Mitogen-activated protein (MAP) kinase and the ribosomal protein S6 kinase. Neither hepsin nor pro-MSP alone was effective in activating Ron signaling pathway, while the hepsin-treated pro-MSP showed robust phosphorylation of both MAP kinase and S6 kinase in a dose dependent manner. The extent of phosphorylation in hepsin-treated pro-MSP was comparable to that of a mature MSP sample from a commercial source.

Peritoneal Macrophage Morphology Change and Chemotaxis Assay

Figure 5:
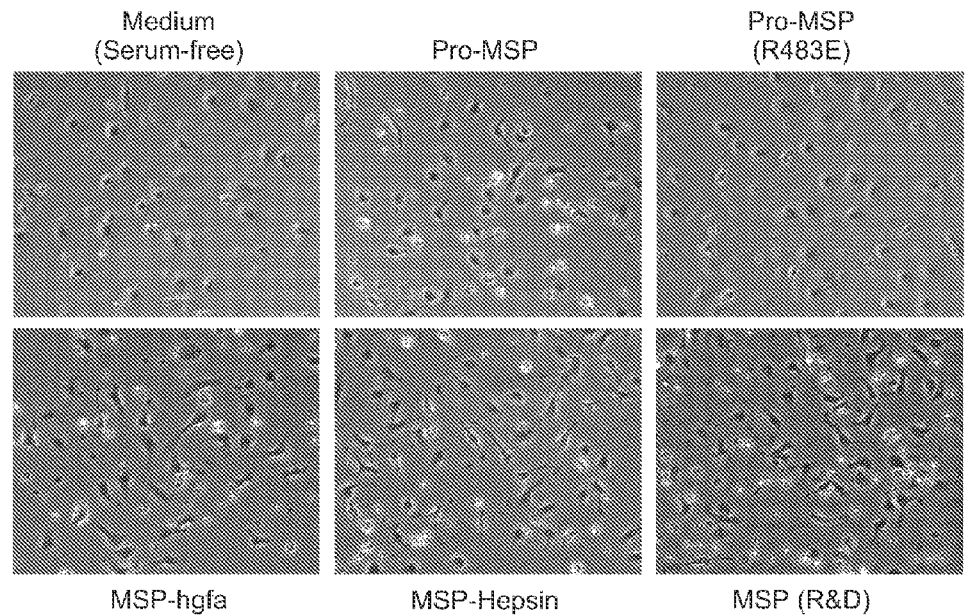
FIG. 5: Peritoneal macrophage morphology change assay. Upon stimulation with hepsin-activated MSP, peritoneal macrophages underwent distinct changes in cell shape, demonstrated by protrusion and elongation. The effect of hepsin-activated MSP was comparable with that of a commercially available MSP as well as HGFA-activated MSP.

The biological activity of hepsin-activated MSP was further assessed in primary macrophage cultures. Mature MSP is known to cause characteristic morphological changes in macrophages. Upon stimulation with hepsin-activated MSP, peritoneal macrophages underwent distinct changes in cell shape, demonstrated by protrusion and elongation (FIG. 5). The effect of hepsin-activated MSP was comparable with that of a commercially available MSP as well as HGFA-activated MSP.

Figure 6:
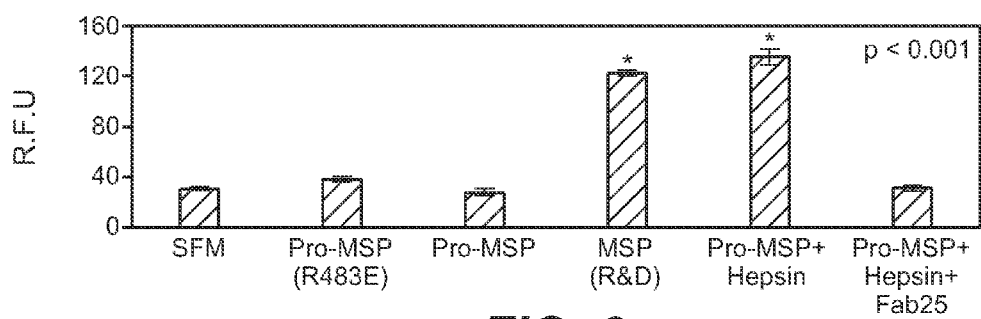
FIG. 6: Chemotaxis assay. Treatment of pro-MSP with hepsin led to a significant increase (p<0.001) in the migration of peritoneal macrophages and the effect was comparable to mature MSP from a commercial source. Pre-treatment with an anti-hepsin inhibitor (anti-hepsin antibody Fab25) displayed marked reduction in the migration of macrophages.

In a chemotaxis assay, treatment of pro-MSP with hepsin led to a significant increase (p<0.001) in the migration of peritoneal macrophages (FIG. 6) and the effect was comparable to mature MSP from a commercial source. Pre-treatment with an anti-hepsin inhibitor displayed marked reduction in the migration of macrophages.

Inhibition of Nitric Oxide (NO) Synthesis

Figure 7:
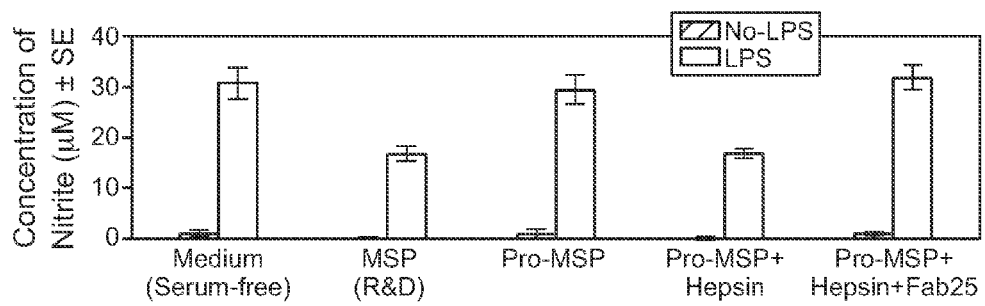
FIG. 7: Inhibition of nitric oxide synthesis. Primary mouse bone marrow macrophages showed a robust production of nitric oxide in response to LPS. Hepsin-activated MSP significantly attenuated the NO production in bone-marrow derived macrophages. The effect of hepsin-activated MSP was comparable with that of a commercially available MSP. Treatment with pro-MSP or pro-MSP mixed with hepsin and anti-hepsin antibody Fab25 did not inhibit robust production of nitric oxide in response to LPS.

Wang et al have previously shown that mature MSP is capable of blocking the increase in macrophage nitric oxide synthase mRNA and its associated increase in the production of NO in response to a variety of stimuli (Wang et al., 1994a). Primary mouse bone marrow macrophages showed a robust production of nitric oxide in response to LPS. Hepsin-activated MSP significantly attenuated the NO production in bone-marrow derived macrophages (FIG. 7) and this effect was completely inhibited in the presence of the anti-hepsin antibody, whereas the pro-MSP alone did not inhibit this response.

Partial Reference List

Betsunoh H, Mukai S, Akiyama Y, Fukushima T, Minamiguchi N, Hasui Y, Osada Y and Kataoka H. (2007). Cancer Sci, 98, 491-498.

Bhatt A S, Welm A, Farady C J, Vasquez M, Wilson K and Craik C S. (2007). Proc Natl Acad Sci USA, 104, 5771-6.

Dhanasekaran S M, Barrette T R, Ghosh D, Shah R, Varambally S, Kurachi K, Pienta K J, Rubin M A and Chinnaiyan A M. (2001). Nature, 412, 822-6.

Herter S, Piper D E, Aaron W, Gabriele T, Cutler G, Cao P, Bhatt A S, Choe Y, Craik C S, Walker N, Meininger D, Hoey T and Austin R J. (2005). Biochem J, 390, 125-36.

Kawaguchi M, Orikawa H, Baba T, Fukushima T and Kataoka H. (2009). Febs J, 276, 3481-90.

Kazama Y, Hamamoto T, Foster D C and Kisiel W. (1995). J Biol Chem, 270, 66-72. Kirchhofer D, Peek M, Lipari M T, Billeci K, Fan B and Moran P. (2005). FEBS Lett, 579, 1945-50.

Leonard E J and Danilkovitch A. (2000). Adv Cancer Res, 77, 139-67.

Luo J, Duggan D J, Chen Y, Sauvageot J, Ewing C M, Bittner M L, Trent J M and Isaacs W B. (2001). Cancer Res, 61, 4683-8.

Magee J A, Araki T, Patil S, Ehrig T, True L, Humphrey P A, Catalona W J, Watson M A and Milbrandt J. (2001). Cancer Res, 61, 5692-6.

Matsuo T, Nakamura K, Takamoto N, Kodama J, Hongo A, Abrzua F, Nasu Y, Kumon H and Hiramatsu Y. (2008). Anticancer Res, 28, 159-64.

Moran P, L1 W, Fan B, Vij R, Eigenbrot C and Kirchhofer D. (2006). J Biol Chem, 281, 30439-46.

Morrissey C, True L D, Roudier M P, Coleman 1M, Hawley S, Nelson P S, Coleman R, Wang Y C, Corey E, Lange P H, Higano C S and Vessella R L. (2008). Clin Exp Metastasis, 25, 377-88.

Netzel-Arnett S, Hooper J D, Szabo R, Madison E L, Quigley J P, Bugge T H and Antalis T M. (2003). Cancer Metastasis Rev, 22, 237-58.

Shia S, Stamos J, Kirchhofer D, Fan B, Wu J, Corpuz R T, Santell L, Lazarus R A and Eigenbrot C. (2005). J Mol Biol, 346, 1335-49.

Skeel A, Yoshimura T, Showalter S D, Tanaka S, Appella E and Leonard E J. (1991). J Exp Med, 173, 1227-34.

Stamey T A, Warrington J A, Caldwell M C, Chen Z, Fan Z, Mahadevappa M, McNeal J E, Nolley R and Zhang Z. (2001). J Urol, 166, 2171-7.

Stephan C, Yousef G M, Scorilas A, Jung K, Jung M, Kristiansen G, Hauptmann S, Kishi T, Nakamura T, Loening S A and Diamandis E P. (2004). J Urol, 171, 187-91.

Tanimoto H, Yan Y, Clarke J, Korourian S, Shigemasa K, Parmley T H, Parham G P and O'Brien T J. (1997). Cancer Res, 57, 2884-7.

Tripathi M, Nandana S, Yamashita H, Ganesan R, Kirchhofer D and Quaranta V. (2008). J Biol Chem, 283, 30576-84.

Wagh P K, Peace B E and Waltz S E. (2008). Adv Cancer Res, 100, 1-33.

Wahl R C, Costigan V J, Batac J P, Chen K, Cam L, Courchesne P L, Patterson S D, Zhang K and Pacifici R E. (1997). J Biol Chem, 272, 15053-6.

Wang M H, Cox G W, Yoshimura T, Sheffler L A, Skeel A and Leonard E J. (1994a). J Biol Chem, 269, 14027-31.

Wang M H, Gonias S L, Skeel A, Wolf B B, Yoshimura T and Leonard E J. (1994b). J Biol Chem, 269, 13806-10.

Wang M H, Skeel A and Leonard E J. (1996). J Clin Invest, 97, 720-7.

Wang M H, Yoshimura T, Skeel A and Leonard E J. (1994c). J Biol Chem, 269, 3436-40.

Welsh J B, Sapinoso L M, Su A I, Kern S G, Wang-Rodriguez J, Moskaluk C A, Frierson H F, Jr. and Hampton G M. (2001). Cancer Res, 61, 5974-8.

Wu Q and Parry G. (2007). Front Biosci, 12, 5052-9.

Xuan J A, Schneider D, Toy P, Lin R, Newton A, Zhu Y, Finster S, Vogel D, Mintzer B, Dinter H, Light D, Parry R, Polokoff M, Whitlow M, Wu Q and Parry G. (2006). Cancer Res, 66, 3611-9.

Yoshimura T, Yuhki N, Wang M H, Skeel A and Leonard E J. (1993). J Biol Chem, 268, 15461-8.

Zacharski L R, Ornstein D L, Memoli V A, Rousseau S M and Kisiel W. (1998). Thromb Haemost, 79, 876-7.

Although the foregoing invention has been described in some detail by way of illustration and example for purposes of clarity of understanding, the descriptions and examples should not be construed as limiting the scope of the invention.

We claim:

1. A method of identifying a candidate inhibitor substance that inhibits hepsin activation of pro-macrophage-stimulating protein (pro-MSP), said method comprising: (a) contacting a candidate substance with a first sample comprising hepsin and a pro-MSP substrate, wherein the hepsin is (i) a polypeptide comprising SEQ ID NO:18 or functional fragment thereof or (ii) a polypeptide comprising SEQ ID NO:19 or functional fragment thereof, and wherein the functional fragment of SEQ ID NO:18 is capable of pro-MSP cleavage in a manner similar to SEQ ID NO:18 and the functional fragment of SEQ ID NO:19 is capable of pro-MSP cleavage in a manner similar to SEQ ID NO:19, and wherein the pro-MSP substrate is a polypeptide comprising SEQ ID NO:20 or a functional fragment thereof and wherein the functional fragment of SEQ ID NO:20 comprises Arg483-Val484 peptide linkage and can be activated by hepsin into activated MSP that is capable of activating plasminogen, and (b) comparing amount of pro-MSP substrate activation in the sample with amount of pro-MSP substrate activation in a reference sample comprising the same amount of hepsin and pro-MSP substrate as the first sample but that has not been contacted with said candidate substance, whereby a decrease in amount of pro-MSP substrate activation in the first sample compared to the reference sample indicates that the candidate substance is capable of inhibiting hepsin activation of pro-MSP.

2. The method of claim 1, wherein the hepsin is a polypeptide comprising SEQ ID NO:18 or a functional fragment thereof.

3. The method of claim 2, wherein the hepsin is a polypeptide comprising SEQ ID NO:18.

4. The method of claim 3, wherein the pro-MSP substrate is a polypeide comprising SEQ ID NO:20.

5. The method of claim 2, wherein the pro-MSP substrate is a polypeide comprising SEQ ID NO:20.

6. The method of claim 1, wherein the pro-MSP substrate is a polypeptide comprising SEQ ID NO:20.

7. The method of claim 1, wherein the hepsin is a polypeptide comprising SEQ ID NO:19 or a functional fragment thereof.

8. The method of claim 7, wherein the hepsin is a polypeptide comprising SEQ ID NO:19.

9. The method of claim 8, wherein the pro-MSP substrate is a polypeide comprising SEQ ID NO:20.

10. The method of claim 7, wherein the pro-MSP substrate is a polypeide comprising SEQ ID NO:20.

* * * * *

SEQUENCE LISTING

```
<160> NUMBER OF SEQ ID NOS: 20

<210> SEQ ID NO 1
<211> LENGTH: 5
<212> TYPE: PRT
<213> ORGANISM: Unknown
<220> FEATURE:
<223> OTHER INFORMATION: Description of Unknown: Pro-MSP cleavage
      sequence

<400> SEQUENCE: 1

Ser Lys Leu Arg Val
1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ala Ser Gln Ser Val Ser Ser Ala Val Ala
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

Ser Ala Ser Ser Leu Tyr Ser
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gln Tyr Tyr Ser Ser Tyr Tyr Leu Leu Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Asn Phe Ser Tyr Ser Tyr Met His
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ser Ile Tyr Ser Tyr Tyr Gly Ser Thr Tyr Tyr Ala Asp Ser Val
1               5                   10                  15

Lys Gly

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Arg Ser Asp Ser Trp Ser Tyr Lys Ser Gly Tyr Thr Gln Lys Ile
1               5                   10                  15

Tyr Ser Lys Gly Leu Asp Tyr
            20

<210> SEQ ID NO 8
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

```
Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Ser Tyr Tyr
                 85                  90                  95

Leu Leu Thr Phe Gly Gln Gly Thr Lys Val Glu Ile Lys
                100                 105

<210> SEQ ID NO 9
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Asn Phe Ser Tyr Ser
            20                  25                  30

Tyr Met His Trp Val Arg Gln Ala Pro Gly Lys Gly Leu Glu Trp Val
        35                  40                  45

Ala Ser Ile Tyr Ser Tyr Tyr Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ser Asp Ser Trp Ser Tyr Lys Ser Gly Tyr Thr Gln Lys Ile
                100                 105                 110

Tyr Ser Lys Gly Leu Asp Tyr Trp Gly Gln Gly Thr Leu Val Thr Val
            115                 120                 125

Ser Ser
130

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Gln Leu Arg
1

<210> SEQ ID NO 11
<211> LENGTH: 5
<212> TYPE: PRT
<213> ORGANISM: Unknown
<220> FEATURE:
<223> OTHER INFORMATION: Description of Unknown: ProHGF substrate
      recognition sequence

<400> SEQUENCE: 11

Lys Gln Leu Arg Val
```

-continued

```
<210> SEQ ID NO 12
<211> LENGTH: 5
<212> TYPE: PRT
<213> ORGANISM: Unknown
<220> FEATURE:
<223> OTHER INFORMATION: Description of Unknown: Ln-332 substrate
      recognition sequence

<400> SEQUENCE: 12

Ser Gln Leu Arg Leu
1               5

<210> SEQ ID NO 13
<211> LENGTH: 5
<212> TYPE: PRT
<213> ORGANISM: Unknown
<220> FEATURE:
<223> OTHER INFORMATION: Description of Unknown: Pro-uPA substrate
      recognition sequence

<400> SEQUENCE: 13

Pro Arg Phe Lys Ile
1               5

<210> SEQ ID NO 14
<211> LENGTH: 5
<212> TYPE: PRT
<213> ORGANISM: Unknown
<220> FEATURE:
<223> OTHER INFORMATION: Description of Unknown: FVII substrate
      recognition sequence

<400> SEQUENCE: 14

Pro Gln Gly Arg Ile
1               5

<210> SEQ ID NO 15
<211> LENGTH: 5
<212> TYPE: PRT
<213> ORGANISM: Unknown
<220> FEATURE:
<223> OTHER INFORMATION: Description of Unknown: Pro-tPA substrate
      recognition sequence

<400> SEQUENCE: 15

Pro Gln Phe Arg Ile
1               5

<210> SEQ ID NO 16
<211> LENGTH: 5
<212> TYPE: PRT
<213> ORGANISM: Unknown
<220> FEATURE:
<223> OTHER INFORMATION: Description of Unknown: Plasminogen substrate
      recognition sequence

<400> SEQUENCE: 16

Cys Pro Gly Arg Val
1               5

<210> SEQ ID NO 17
<211> LENGTH: 7
<212> TYPE: PRT
<213> ORGANISM: Homo sapiens

<400> SEQUENCE: 17
```

Val Val Gly Gly His Pro Gly
1               5

<210> SEQ ID NO 18
<211> LENGTH: 417
<212> TYPE: PRT
<213> ORGANISM: Homo sapiens

<400> SEQUENCE: 18

Met Ala Gln Lys Glu Gly Gly Arg Thr Val Pro Cys Cys Ser Arg Pro
1               5                   10                  15

Lys Val Ala Ala Leu Thr Ala Gly Thr Leu Leu Leu Thr Ala Ile
            20                  25                  30

Gly Ala Ala Ser Trp Ala Ile Val Ala Val Leu Leu Arg Ser Asp Gln
            35                  40                  45

Glu Pro Leu Tyr Pro Val Gln Val Ser Ser Ala Asp Ala Arg Leu Met
        50                  55                  60

Val Phe Asp Lys Thr Glu Gly Thr Trp Arg Leu Leu Cys Ser Ser Arg
65                  70                  75                  80

Ser Asn Ala Arg Val Ala Gly Leu Ser Cys Glu Glu Met Gly Phe Leu
                85                  90                  95

Arg Ala Leu Thr His Ser Glu Leu Asp Val Arg Thr Ala Gly Ala Asn
            100                 105                 110

Gly Thr Ser Gly Phe Phe Cys Val Asp Glu Gly Arg Leu Pro His Thr
        115                 120                 125

Gln Arg Leu Leu Glu Val Ile Ser Val Cys Asp Cys Pro Arg Gly Arg
130                 135                 140

Phe Leu Ala Ala Ile Cys Gln Asp Cys Gly Arg Arg Lys Leu Pro Val
145                 150                 155                 160

Asp Arg Ile Val Gly Arg Asp Thr Ser Leu Gly Arg Trp Pro Trp
                165                 170                 175

Gln Val Ser Leu Arg Tyr Asp Gly Ala His Leu Cys Gly Gly Ser Leu
                180                 185                 190

Leu Ser Gly Asp Trp Val Leu Thr Ala Ala His Cys Phe Pro Glu Arg
            195                 200                 205

Asn Arg Val Leu Ser Arg Trp Arg Val Phe Ala Gly Ala Val Ala Gln
        210                 215                 220

Ala Ser Pro His Gly Leu Gln Leu Gly Val Gln Ala Val Val Tyr His
225                 230                 235                 240

Gly Gly Tyr Leu Pro Phe Arg Asp Pro Asn Ser Glu Glu Asn Ser Asn
                245                 250                 255

Asp Ile Ala Leu Val His Leu Ser Ser Pro Leu Pro Leu Thr Glu Tyr
            260                 265                 270

Ile Gln Pro Val Cys Leu Pro Ala Ala Gly Gln Ala Leu Val Asp Gly
        275                 280                 285

Lys Ile Cys Thr Val Thr Gly Trp Gly Asn Thr Gln Tyr Tyr Gly Gln
290                 295                 300

Gln Ala Gly Val Leu Gln Glu Ala Arg Val Pro Ile Ile Ser Asn Asp
305                 310                 315                 320

Val Cys Asn Gly Ala Asp Phe Tyr Gly Asn Gln Ile Lys Pro Lys Met
                325                 330                 335

Phe Cys Ala Gly Tyr Pro Glu Gly Gly Ile Asp Ala Cys Gln Gly Asp
            340                 345                 350

Ser Gly Gly Pro Phe Val Cys Glu Asp Ser Ile Ser Arg Thr Pro Arg
        355                 360                 365

-continued

```
Trp Arg Leu Cys Gly Ile Val Ser Trp Gly Thr Gly Cys Ala Leu Ala
            370                 375                 380

Gln Lys Pro Gly Val Tyr Thr Lys Val Ser Asp Phe Arg Glu Trp Ile
385                 390                 395                 400

Phe Gln Ala Ile Lys Thr His Ser Glu Ala Ser Gly Met Val Thr Gln
                405                 410                 415

Leu

<210> SEQ ID NO 19
<211> LENGTH: 476
<212> TYPE: PRT
<213> ORGANISM: Homo sapiens

<400> SEQUENCE: 19

Met Ala Gln Lys Glu Gly Gly Arg Thr Val Pro Cys Cys Ser Arg Pro
1               5                   10                  15

Lys Val Ala Ala Leu Thr Ala Gly Thr Leu Leu Leu Thr Ala Ile
            20                  25                  30

Gly Ala Ala Ser Trp Ala Ile Val Ala Val Leu Leu Arg Ser Asp Gln
        35                  40                  45

Glu Pro Leu Tyr Pro Val Gln Val Ser Ala Asp Ala Arg Leu Met
    50                  55                  60

Val Phe Asp Lys Thr Glu Gly Thr Trp Arg Leu Leu Cys Ser Ser Arg
65                  70                  75                  80

Ser Asn Ala Arg Val Ala Gly Leu Ser Cys Glu Glu Met Gly Phe Leu
                85                  90                  95

Arg Ala Leu Thr His Ser Glu Leu Asp Val Arg Thr Ala Gly Ala Asn
            100                 105                 110

Gly Thr Ser Gly Phe Phe Cys Val Asp Glu Gly Arg Leu Pro His Thr
        115                 120                 125

Gln Arg Leu Leu Glu Val Ile Ser Val Cys Asp Cys Pro Arg Gly Arg
    130                 135                 140

Phe Leu Ala Ala Ile Cys Gln Gly Glu Ile Leu Lys Leu Arg Thr Leu
145                 150                 155                 160

Ser Phe Arg Pro Leu Gly Arg Pro Arg Pro Leu Lys Leu Pro Arg Met
                165                 170                 175

Gly Pro Cys Thr Phe Arg Pro Arg Ala Gly Pro Ser Leu Gly Ser
            180                 185                 190

Gly Asp Leu Gly Ser Ser Pro Leu Ser Pro Pro Ala Asp Pro Cys
        195                 200                 205

Pro Thr Asp Cys Gly Arg Arg Lys Leu Pro Val Asp Arg Ile Val Gly
    210                 215                 220

Gly Arg Asp Thr Ser Leu Gly Arg Trp Pro Trp Gln Val Ser Leu Arg
225                 230                 235                 240

Tyr Asp Gly Ala His Leu Cys Gly Gly Ser Leu Leu Ser Gly Asp Trp
                245                 250                 255

Val Leu Thr Ala Ala His Cys Phe Pro Glu Arg Asn Arg Val Leu Ser
            260                 265                 270

Arg Trp Arg Val Phe Ala Gly Ala Val Ala Gln Ala Ser Pro His Gly
        275                 280                 285

Leu Gln Leu Gly Val Gln Ala Val Val Tyr His Gly Gly Tyr Leu Pro
    290                 295                 300

Phe Arg Asp Pro Asn Ser Glu Glu Asn Ser Asn Asp Ile Ala Leu Val
305                 310                 315                 320

His Leu Ser Ser Pro Leu Pro Leu Thr Glu Tyr Ile Gln Pro Val Cys
```

```
                   325                 330                 335
Leu Pro Ala Ala Gly Gln Ala Leu Val Asp Gly Lys Ile Cys Thr Val
            340                 345                 350

Thr Gly Trp Gly Asn Thr Gln Tyr Tyr Gly Gln Gln Ala Gly Val Leu
            355                 360                 365

Gln Glu Ala Arg Val Pro Ile Ile Ser Asn Asp Val Cys Asn Gly Ala
            370                 375                 380

Asp Phe Tyr Gly Asn Gln Ile Lys Pro Lys Met Phe Cys Ala Gly Tyr
385                 390                 395                 400

Pro Glu Gly Gly Ile Asp Ala Cys Gln Gly Asp Ser Gly Gly Pro Phe
                405                 410                 415

Val Cys Glu Asp Ser Ile Ser Arg Thr Pro Arg Trp Arg Leu Cys Gly
            420                 425                 430

Ile Val Ser Trp Gly Thr Gly Cys Ala Leu Ala Gln Lys Pro Gly Val
            435                 440                 445

Tyr Thr Lys Val Ser Asp Phe Arg Glu Trp Ile Phe Gln Ala Ile Lys
            450                 455                 460

Thr His Ser Glu Ala Ser Gly Met Val Thr Gln Leu
465                 470                 475

<210> SEQ ID NO 20
<211> LENGTH: 711
<212> TYPE: PRT
<213> ORGANISM: Homo sapiens

<400> SEQUENCE: 20

Met Gly Trp Leu Pro Leu Leu Leu Leu Thr Gln Cys Leu Gly Val
1               5                   10                  15

Pro Gly Gln Arg Ser Pro Leu Asn Asp Phe Gln Val Leu Arg Gly Thr
            20                  25                  30

Glu Leu Gln His Leu Leu His Ala Val Val Pro Gly Pro Trp Gln Glu
            35                  40                  45

Asp Val Ala Asp Ala Glu Glu Cys Ala Gly Arg Cys Gly Pro Leu Met
        50                  55                  60

Asp Cys Arg Ala Phe His Tyr Asn Val Ser Ser His Gly Cys Gln Leu
65                  70                  75                  80

Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
            100                 105                 110

Asn Asn Gly Val Gly Tyr Arg Gly Thr Met Ala Thr Thr Val Gly Gly
            115                 120                 125

Leu Pro Cys Gln Ala Trp Ser His Lys Phe Pro Asn Asp His Lys Tyr
        130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
            180                 185                 190

Trp Cys Asn Gly Glu Glu Tyr Arg Gly Ala Val Asp Arg Thr Glu Ser
            195                 200                 205

Gly Arg Glu Cys Gln Arg Trp Asp Leu Gln His Pro His Gln His Pro
        210                 215                 220

Phe Glu Pro Gly Lys Phe Leu Asp Gln Gly Leu Asp Asp Asn Tyr Cys
```

-continued

```
                225                 230                 235                 240
Arg Asn Pro Asp Gly Ser Glu Arg Pro Trp Cys Tyr Thr Thr Asp Pro
                    245                 250                 255
Gln Ile Glu Arg Glu Phe Cys Asp Leu Pro Arg Cys Gly Ser Glu Ala
                260                 265                 270
Gln Pro Arg Gln Glu Ala Thr Thr Val Ser Cys Phe Arg Gly Lys Gly
            275                 280                 285
Glu Gly Tyr Arg Gly Thr Ala Asn Thr Thr Ala Gly Val Pro Cys
        290                 295                 300
Gln Arg Trp Asp Ala Gln Ile Pro His Gln His Arg Phe Thr Pro Glu
305                 310                 315                 320
Lys Tyr Ala Cys Lys Asp Leu Arg Glu Asn Phe Cys Arg Asn Pro Asp
                325                 330                 335
Gly Ser Glu Ala Pro Trp Cys Phe Thr Leu Arg Pro Gly Met Arg Ala
                340                 345                 350
Ala Phe Cys Tyr Gln Ile Arg Arg Cys Thr Asp Asp Val Arg Pro Gln
            355                 360                 365
Asp Cys Tyr His Gly Ala Gly Glu Gln Tyr Arg Gly Thr Val Ser Lys
        370                 375                 380
Thr Arg Lys Gly Val Gln Cys Gln Arg Trp Ser Ala Glu Thr Pro His
385                 390                 395                 400
Lys Pro Gln Phe Thr Phe Thr Ser Glu Pro His Ala Gln Leu Glu Glu
                405                 410                 415
Asn Phe Cys Arg Asn Pro Asp Gly Asp Ser His Gly Pro Trp Cys Tyr
                420                 425                 430
Thr Met Asp Pro Arg Thr Pro Phe Asp Tyr Cys Ala Leu Arg Arg Cys
            435                 440                 445
Ala Asp Asp Gln Pro Pro Ser Ile Leu Asp Pro Pro Asp Gln Val Gln
        450                 455                 460
Phe Glu Lys Cys Gly Lys Arg Val Asp Arg Leu Asp Gln Arg Arg Ser
465                 470                 475                 480
Lys Leu Arg Val Val Gly Gly His Pro Gly Asn Ser Pro Trp Thr Val
                485                 490                 495
Ser Leu Arg Asn Arg Gln Gly Gln His Phe Cys Gly Gly Ser Leu Val
                500                 505                 510
Lys Glu Gln Trp Ile Leu Thr Ala Arg Gln Cys Phe Ser Ser Cys His
            515                 520                 525
Met Pro Leu Thr Gly Tyr Glu Val Trp Leu Gly Thr Leu Phe Gln Asn
        530                 535                 540
Pro Gln His Gly Glu Pro Ser Leu Gln Arg Val Pro Val Ala Lys Met
545                 550                 555                 560
Val Cys Gly Pro Ser Gly Ser Gln Leu Val Leu Leu Lys Leu Glu Arg
                565                 570                 575
Ser Val Thr Leu Asn Gln Arg Val Ala Leu Ile Cys Leu Pro Pro Glu
                580                 585                 590
Trp Tyr Val Val Pro Pro Gly Thr Lys Cys Glu Ile Ala Gly Trp Gly
            595                 600                 605
Glu Thr Lys Gly Thr Gly Asn Asp Thr Val Leu Asn Val Ala Leu Leu
        610                 615                 620
Asn Val Ile Ser Asn Gln Glu Cys Asn Ile Lys His Arg Gly Arg Val
625                 630                 635                 640
Arg Glu Ser Glu Met Cys Thr Glu Gly Leu Leu Ala Pro Val Gly Ala
                645                 650                 655
```

```
                                      -continued
Cys Glu Gly Asp Tyr Gly Gly Pro Leu Ala Cys Phe Thr His Asn Cys
            660                 665                 670

Trp Val Leu Glu Gly Ile Ile Ile Pro Asn Arg Val Cys Ala Arg Ser
        675                 680                 685

Arg Trp Pro Ala Val Phe Thr Arg Val Ser Val Phe Val Asp Trp Ile
    690                 695                 700

His Lys Val Met Arg Leu Gly
705                 710
```